(12) United States Patent
McKearn et al.

(10) Patent No.: US 6,689,787 B1
(45) Date of Patent: Feb. 10, 2004

(54) METHOD OF USING AN INTEGRIN ANTAGONIST AND RADIATION THERAPY AS COMBINATION THERAPY IN THE TREATMENT OF NEOPLASIA

(75) Inventors: John P. McKearn, Glencoe, MO (US); Gary Gordon, Highland, IL (US); James J. Cunningham, Chicago, IL (US); Stephen T. Gately, Palatine, IL (US); Alane T. Koki, Beaufort, MO (US); Jaime L. Masferrer, Ballwin, MO (US)

(73) Assignee: G. D. Searle & Co., Skokie, IL (US)

( * ) Notice: Subject to any disclaimer, the term of this patent is extended or adjusted under 35 U.S.C. 154(b) by 0 days.

(21) Appl. No.: 09/857,871

(22) PCT Filed: Dec. 22, 1999

(86) PCT No.: PCT/US99/30621

§ 371 (c)(1),
(2), (4) Date: Oct. 5, 2001

(87) PCT Pub. No.: WO00/38715

PCT Pub. Date: Jul. 6, 2000

Related U.S. Application Data

(60) Provisional application No. 60/113,786, filed on Dec. 23, 1998.

(51) Int. Cl.[7] ............................................. A61K 31/505
(52) U.S. Cl. ..................... 514/275; 514/398; 514/352; 514/300; 514/299; 514/183; 514/395; 514/565; 514/538; 514/397
(58) Field of Search ................ 514/275, 398, 514/565, 395, 352, 300, 298, 183, 538, 397

(56) References Cited

U.S. PATENT DOCUMENTS

| | | | |
|---|---|---|---|
| 4,472,382 A | 9/1984 | Labrie et al. ............. 424/177 |
| 4,596,797 A | 6/1986 | Schweikert et al. ........ 514/177 |
| 4,659,695 A | 4/1987 | Labrie ..................... 514/15 |
| 4,760,053 A | 7/1988 | Labrie ..................... 514/15 |
| 4,775,660 A | 10/1988 | Labrie et al. .............. 514/15 |
| 5,039,805 A | 8/1991 | Alig et al. ................ 546/224 |
| 5,061,693 A | 10/1991 | Nutt et al. ................. 514/17 |
| 5,225,531 A | 7/1993 | Gresham et al. ........... 530/329 |
| 5,229,366 A | 7/1993 | Tsukad et al. .............. 514/12 |
| 5,464,855 A | 11/1995 | Capiris et al. .............. 514/382 |
| 5,491,129 A | 2/1996 | Shaltiel et al. ............. 514/12 |
| 5,510,332 A | 4/1996 | Kogan et al. ............... 514/14 |
| 5,536,814 A | 7/1996 | Ruoslahti et al. ........... 530/329 |
| 5,565,449 A | 10/1996 | Blackburn et al. .......... 514/219 |
| 5,574,026 A | 11/1996 | Backer et al. .............. 514/152 |
| 5,612,311 A | 3/1997 | Pierschbacher et al. ...... 514/11 |
| 5,627,197 A | 5/1997 | Gante et al. ............... 514/326 |
| 5,639,726 A | 6/1997 | Lawrence et al. ........... 514/12 |
| 5,663,297 A | 9/1997 | Alig et al. ................ 530/331 |
| 5,686,566 A | 11/1997 | Scarborough et al. ....... 530/329 |
| 5,686,567 A | 11/1997 | Scarborough et al. ....... 530/329 |
| 5,686,568 A | 11/1997 | Scarborough et al. ....... 530/329 |
| 5,686,569 A | 11/1997 | Scarborough et al. ....... 530/329 |
| 5,686,570 A | 11/1997 | Scarborough et al. ....... 530/329 |
| 5,686,571 A | 11/1997 | Scarborough et al. ....... 530/329 |
| 5,721,210 A | 2/1998 | Lobl et al. ................. 514/11 |
| 5,741,796 A | 4/1998 | Hartman et al. ............ 514/300 |
| 5,759,996 A | 6/1998 | Cheng et al. ............... 514/11 |
| 5,760,028 A | 6/1998 | Jadhav et al. .............. 514/211 |
| 5,766,591 A * | 6/1998 | Brooks et al. ............ 424/184.1 |
| 5,773,412 A | 6/1998 | Cheng et al. ............... 514/11 |
| 5,773,644 A | 6/1998 | Chen et al. ................ 562/439 |
| 5,773,646 A | 6/1998 | Chandrakumar et al. ... 562/439 |
| 5,840,961 A | 11/1998 | Behling et al. ............. 560/172 |
| 5,843,906 A | 12/1998 | Chandrakumar et al. .... 514/19 |
| 5,852,210 A | 12/1998 | Chen et al. ................ 562/439 |
| 5,863,538 A | 1/1999 | Thorpe et al. ............. 424/136.1 |
| 5,912,234 A | 6/1999 | Ruoslahti et al. ........... 514/17 |
| 5,919,792 A | 7/1999 | Duggan et al. ............. 514/300 |
| 5,925,655 A | 7/1999 | Duggan et al. ............. 514/333 |
| 5,952,381 A | 9/1999 | Chen et al. ................ 514/565 |
| 5,955,572 A | 9/1999 | Ruoslahti et al. ........... 530/317 |
| 6,013,651 A | 1/2000 | Rogers et al. .............. 514/269 |
| 6,017,925 A * | 1/2000 | Duggan ..................... 514/300 |
| 6,028,223 A | 2/2000 | Ruminski et al. ............ 564/27 |
| 6,040,311 A * | 3/2000 | Duggan et al. ............. 514/275 |
| 6,100,423 A | 8/2000 | Collins et al. .............. 560/42 |
| 6,251,944 B1 | 6/2001 | Chen et al. ................ 514/565 |
| 6,372,719 B1 * | 4/2002 | Cunningham et al. ........ 514/34 |

FOREIGN PATENT DOCUMENTS

| | | |
|---|---|---|
| CA | 21/20303 | 10/1994 |
| DE | 4310643 | 10/1994 |
| DE | 4336758 | 5/1995 |
| DE | 4415310 | 11/1995 |
| DE | 4439846 | 5/1996 |
| DE | 19548798 | 7/1997 |
| DE | 19613933 | 10/1997 |
| DE | 19626701 | 1/1998 |
| DE | 19654483 | 1/1998 |
| DE | 19653645 | 6/1998 |
| DE | 19653647 | 6/1998 |
| EP | 372486 | 12/1989 |
| EP | 381033 | 1/1990 |
| EP | 384362 | 2/1990 |
| EP | 410767 | 7/1990 |
| EP | 445796 | 3/1991 |
| EP | 529858 | 8/1992 |

(List continued on next page.)

OTHER PUBLICATIONS

U.S. patent application Ser. No. 09/141,547, Chandrakumar et al., filed Aug. 28, 1998.

McDonald et al, Alopecia & Cutaneous Complications; Clinical Oncology; 753–770; 1992.

(List continued on next page.)

Primary Examiner—James H. Reamer
(74) Attorney, Agent, or Firm—Thomas R. Stiebel, Jr.; Rachel A. Polster

(57) ABSTRACT

The present invention provides methods to treat neoplasia disorders in a mammal using a combination of radiation and an integrin antagonist.

15 Claims, No Drawings

FOREIGN PATENT DOCUMENTS

| | | |
|---|---|---|
| EP | 537654 | 10/1992 |
| EP | 570352 | 4/1993 |
| EP | 589181 | 7/1993 |
| EP | 614664 | 3/1994 |
| EP | 618225 | 3/1994 |
| EP | 632053 | 3/1994 |
| EP | 62/3615 | 4/1994 |
| EP | 0645376 | 9/1994 |
| EP | 656348 | 11/1994 |
| EP | 668278 | 2/1995 |
| EP | 683173 | 4/1995 |
| EP | 0710657 | 10/1995 |
| EP | 711770 | 10/1995 |
| EP | 727425 | 2/1996 |
| EP | 741133 | 4/1996 |
| EP | 77/0622 | 8/1996 |
| EP | 765660 | 9/1996 |
| EP | 77/1818 | 9/1996 |
| EP | 0771565 | 10/1996 |
| EP | 796855 | 3/1997 |
| EP | 771565 | 5/1997 |
| EP | 820988 | 7/1997 |
| EP | 820991 | 7/1997 |
| EP | 0846702 | 11/1997 |
| EP | 853084 | 12/1997 |
| EP | 854140 | 12/1997 |
| EP | 854145 | 12/1997 |
| EP | 710657 | 8/1998 |
| EP | 928793 | 12/1998 |
| EP | 645376 | 4/1999 |
| JP | 5163293 | 12/1991 |
| JP | 06116289 | 4/1994 |
| JP | 07206860 | 8/1995 |
| JP | 07242645 | 9/1995 |
| JP | 07285992 | 10/1995 |
| JP | 08183752 | 7/1996 |
| JP | 08183788 | 7/1996 |
| JP | 08337523 | 12/1996 |
| JP | 09169742 | 6/1997 |
| JP | 9235239 | 9/1997 |
| JP | 09235239 | 9/1997 |
| JP | 09316000 | 12/1997 |
| JP | 10045587 | 2/1998 |
| WO | 94/05310 | 3/1974 |
| WO | 89/05155 | 6/1989 |
| WO | 90/03983 | 4/1990 |
| WO | 91/07977 | 6/1991 |
| WO | 91/15515 | 10/1991 |
| WO | 92/00995 | 1/1992 |
| WO | 92/07870 | 5/1992 |
| WO | 92/09200 | 6/1992 |
| WO | 93/08174 | 4/1993 |
| WO | 93/18652 | 9/1993 |
| WO | 93/20229 | 10/1993 |
| WO | 93/25218 | 12/1993 |
| WO | 94/01152 | 1/1994 |
| WO | 94/11739 | 5/1994 |
| WO | 94/13310 | 6/1994 |
| WO | 94/15936 | 7/1994 |
| WO | 94/18981 | 9/1994 |
| WO | 94/21607 | 9/1994 |
| WO | 95/00544 | 1/1995 |
| WO | 95/07712 | 3/1995 |
| WO | 95/14714 | 6/1995 |
| WO | 95/23811 | 9/1995 |
| WO | 95/25543 | 9/1995 |
| WO | 95/28426 | 10/1995 |
| WO | 95/30438 | 11/1995 |
| WO | 95/32710 | 12/1995 |
| WO | 95/34641 | 12/1995 |
| WO | 96/00574 | 1/1996 |
| WO | 96/00581 | 1/1996 |
| WO | 96/00730 | 1/1996 |
| WO | 96/01653 | 1/1996 |
| WO | 96/05304 | 2/1996 |
| WO | 96/06087 | 2/1996 |
| WO | 96/07734 | 3/1996 |
| WO | 96/16983 | 6/1996 |
| WO | 96/21416 | 7/1996 |
| WO | 96/26190 | 8/1996 |
| WO | 96/32945 | 10/1996 |
| WO | 96/37492 | 11/1996 |
| WO | 96/40250 | 12/1996 |
| WO | 96/40781 | 12/1996 |
| WO | 97/01540 | 1/1997 |
| WO | 97/03094 | 1/1997 |
| WO | 97/06791 | 2/1997 |
| WO | 97/08145 | 3/1997 |
| WO | 97/08203 | 3/1997 |
| WO | 97/10507 | 3/1997 |
| WO | 97/11718 | 4/1997 |
| WO | 97/12625 | 4/1997 |
| WO | 97/14716 | 4/1997 |
| WO | 97/15666 | 5/1997 |
| WO | 97/16197 | 5/1997 |
| WO | 97/18838 | 5/1997 |
| WO | 97/21726 | 6/1997 |
| WO | 97/22596 | 6/1997 |
| WO | 97/23451 | 7/1997 |
| WO | 97/23480 | 7/1997 |
| WO | 97/23625 | 7/1997 |
| WO | 97/24119 | 7/1997 |
| WO | 97/24122 | 7/1997 |
| WO | 97/24124 | 7/1997 |
| WO | 97/24336 | 7/1997 |
| WO | 97/25031 | 7/1997 |
| WO | 97/26250 | 7/1997 |
| WO | 97/26258 | 7/1997 |
| WO | 97/33576 | 9/1997 |
| WO | 97/33887 | 9/1997 |
| WO | 97/34865 | 9/1997 |
| WO | 97/34876 | 9/1997 |
| WO | 97/35615 | 10/1997 |
| WO | 97/36858 | 10/1997 |
| WO | 97/36859 | 10/1997 |
| WO | 97/36860 | 10/1997 |
| WO | 97/36861 | 10/1997 |
| WO | 97/36862 | 10/1997 |
| WO | 97/37655 | 10/1997 |
| WO | 97/39028 | 10/1997 |
| WO | 97/41102 | 11/1997 |
| WO | 97/41149 | 11/1997 |
| WO | WO9741844 | 11/1997 |
| WO | 97/41844 | 11/1997 |
| WO | 97/44333 | 11/1997 |
| WO | 97/45137 | 11/1997 |
| WO | 97/45447 | 12/1997 |
| WO | 97/48395 | 12/1997 |
| WO | 97/48444 | 12/1997 |
| WO | 98/00144 | 1/1998 |
| WO | 98/00395 | 1/1998 |
| WO | 98/03573 | 1/1998 |
| WO | 98/04913 | 2/1998 |
| WO | 98/07432 | 2/1998 |
| WO | 98/08518 | 3/1998 |
| WO | 98/08840 | 3/1998 |
| WO | 98/10795 | 3/1998 |
| WO | 98/11089 | 3/1998 |
| WO | 98/11223 | 3/1998 |
| WO | 98/12226 | 3/1998 |
| WO | 98/13071 | 4/1998 |

| | | |
|---|---|---|
| WO | 98/13350 | 4/1998 |
| WO | 98/13354 | 4/1998 |
| WO | 98/14192 | 4/1998 |
| WO | 98/15278 | 4/1998 |
| WO | 98/15574 | 4/1998 |
| WO | 98/16227 | 4/1998 |
| WO | 98/18460 | 5/1998 |
| WO | 98/18461 | 5/1998 |
| WO | 98/18764 | 5/1998 |
| WO | 98/20897 | 5/1998 |
| WO | 98/21230 | 5/1998 |
| WO | 98/22500 | 5/1998 |
| WO | 98/23608 | 6/1998 |
| WO | 98/23613 | 6/1998 |
| WO | 98/25601 | 6/1998 |
| WO | 98/25892 | 6/1998 |
| WO | 98/30542 | 7/1998 |
| WO | 98/31359 | 7/1998 |
| WO | WO9831359 | 7/1998 |
| WO | 98/33919 | 8/1998 |
| WO | 98/34918 | 8/1998 |
| WO | WO9814192 | 9/1998 |
| WO | 98/43962 | 10/1998 |
| WO | 98/54217 | 12/1998 |
| WO | 99/05107 | 2/1999 |
| WO | 99/06049 | 2/1999 |
| WO | 99/11626 | 3/1999 |
| WO | 99/15170 | 4/1999 |
| WO | 99/15178 | 4/1999 |
| WO | 99/15506 | 4/1999 |
| WO | 99/15507 | 4/1999 |
| WO | 99/15508 | 4/1999 |
| WO | 99/21583 | 5/1999 |
| WO | 99/26945 | 6/1999 |
| WO | 99/30709 | 6/1999 |
| WO | 99/30713 | 6/1999 |
| WO | 99/31061 | 6/1999 |
| WO | 99/31099 | 6/1999 |
| WO | WO9931099 | 6/1999 |
| WO | 99/32457 | 7/1999 |
| WO | 99/33798 | 7/1999 |
| WO | 99/37621 | 7/1999 |
| WO | 99/37683 | 7/1999 |
| WO | 99/38849 | 8/1999 |
| WO | 99/44994 | 9/1999 |
| WO | 99/45927 | 9/1999 |
| WO | WO9942896 | 10/1999 |
| WO | 99/50249 | 10/1999 |

OTHER PUBLICATIONS

Hellman ; Principles of Radiation therapy, Cancer in Principles and Practice fo Oncology ; 248–75.
European Group on Tumor markers Publications Committee; Consensus Recommendations; Anticancer Research; 19; 2785–2820; 1999.
Cellular Markers of Cancer; Carleton Garrett & Stewart Sell; Totowa, NJ; Human Press; 1995.
A.F. Horwitz; Scientific American; 276(5); 68–75; 1997.
M. Pfaff et al; Cell Adhes Commun; 2(6); 491–501; 1994.
Healy, J.M. et al; Protein Pept Lett; 3(1); 23–30; 1996.
Hart, S.L. et al; J. Biol. Chem.; 269(17); 12468–12474; 1994.
M. Pfaff et al; J. Biol. Chem; 269(32); 20233–20238; 1994.
D.A. Cheresh et al; J. Biol. Chem. 262(36); 17703–17711; 1987.
Seftor et al; Proc Nat'l Acad Sci USA; 89; 1557–1561; 1992.
Montgomery et al; Proc Nat'l Acad Sci USA; 91; 8856–8860; 1994.
Brooks et al; Cell; 79; 1157–1164; 1994.
Adonis et al; Amer. J. Opthal.; 118; 445–450; 1994.
Peacock et al; J. Exp. Med; 175; 1135–1138; 1992.
Brooks et al; Science; 264; 569–571; 1994.
J. Clin. Oncol; 10; 829–838; 1992.
Pharmacology; 41; 177–183; 1990.
Tetragenesis, Carcinogenesis, & Mutagenesis; 10; 477–501; 1990.
Haskel, Chest; 99; 1325; 1991.
Bakowsk, Cancer Treat Rev; 10; 159; 1983.
Joss, Cancer Treat Rev; 11; 205; 1984.
Ihde, Cancer; 54; 2722; 1984.

* cited by examiner

METHOD OF USING AN INTEGRIN ANTAGONIST AND RADIATION THERAPY AS COMBINATION THERAPY IN THE TREATMENT OF NEOPLASIA

This application is a 371 of PCT US99/30621 filed Dec. 22, 1999. This application claims the benefit of U.S. provisional application Ser. No. 60/113,786 filed Dec. 23, 1998.

FIELD OF THE INVENTION

The present invention relates to a combination of radiation therapy and an integrin antagonist for treatment of neoplasia disorders. More specifically, this invention relates to the use of integrin antagonists in combination with radiation therapy for treating cancer.

BACKGROUND OF THE INVENTION

A neoplasm, or tumor, is an abnormal, unregulated, and disorganized proliferation of cell growth. A neoplasm is malignant, or cancerous, if it has properties of destructive growth, invasiveness and metastasis. Invasiveness refers to the local spread of a neoplasm by infiltration or destruction of surrounding tissue, typically breaking through the basal laminas that define the boundaries of the tissues, thereby often entering the body's circulatory system. Metastasis typically refers to the dissemination of tumor cells by lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

Cancer is now the second leading cause of death in the United States and over 8,000,000 persons in the United States have been diagnosed with cancer. In 1995, cancer accounted for 23.3% of all deaths in the United States.

Cancer is not fully understood on the molecular level. It is known that exposure of a cell to a carcinogen such as certain viruses, certain chemicals, or radiation, leads to DNA alteration that inactivates a suppressive gene or activates an "oncogene". Suppressive genes are growth regulatory genes, which upon mutation, can no longer control cell growth. Oncogenes are initially normal genes (called proto-oncogenes) that by mutation or altered context of expression become transforming genes. The products of transforming genes cause inappropriate cell growth. More than twenty different normal cellular genes can become oncogenes by genetic alteration. Transformed cells differ from normal cells in many ways, including cell morphology, cell-to-cell interactions, membrane content, cytoskeletal structure, protein secretion, gene expression and mortality.

Cancer is now primarily treated with one or a combination of three types of therapies: surgery, radiation, and chemotherapy. Surgery involves the bulk removal of diseased tissue. While surgery is sometimes effective in removing tumors located at certain sites, for example, in the breast, colon, and skin, it cannot be used in the treatment of tumors located in other areas, inaccessible to surgeons, nor in the treatment of disseminated neoplastic conditions such as leukemia.

Chemotherapy involves the disruption of cell replication or cell metabolism. It is used most often in the treatment of breast, lung, and testicular cancer.

The adverse effects of systemic chemotherapy used in the treatment of neoplastic disease is most feared by patients undergoing treatment for cancer. Of these adverse effects nausea and vomiting are the most common and severe side effects. Other adverse side effects include cytopenia, infection, cachexia, mucositis in patients receiving high doses of chemotherapy with bone marrow rescue or radiation therapy; alopecia (hair loss); cutaneous complications such as pruritus, urticaria, and angioedema; neurological complications; pulmonary and cardiac complications in patients receiving radiation or chemotherapy; and reproductive and endocrine complications (M. Abeloff, et al., Alopecia and Cutaneous Complications, in Clinical Oncology 755–56 (Abeloff, ed. 1992).

Chemotherapy-induced side effects significantly impact the quality of life of the patient and may dramatically influence patient compliance with treatment.

Additionally, adverse side effects associated with chemotherapeutic agents are generally the major dose-limiting toxicity (DLT) in the administration of these drugs. For example, mucositis, is one of the major dose limiting toxicity for several anticancer agents, including the antimetabolite cytotoxic agents 5-FU, methotrexate, and antitumor antibiotics, such as doxorubicin. Many of these chemotherapy-induced side effects if severe, may lead to hospitalization, or require treatment with analgesics for the treatment of pain.

In general, radiation therapy is employed as potentially curative therapy for patients who present with clinically localized disease and are expected to live at least 10 years. For example, approximately 70% of newly diagnosed prostate cancer patients fall into this category.

Approximately 10% of these patients (7% of total patients) undergo radiation therapy. Approximately 80% of patients who have undergone radiation as their primary therapy have disease persistence or develop recurrence or metastasis within five years after treatment. Currently, most of these radiotherapy patients generally do not receive any immediate follow-up therapy. Rather, they are monitored frequently, such as for elevated Prostate Specific Antigen ("PSA"), which is the primary indicator of recurrence or metastasis in prostate cancer.

The adverse side effects induced by chemotherapeutic agents and radiation therapy have become of major importance to the clinical management of cancer patients.

Colorectal Cancer

Survival from colorectal cancer depends on the stage and grade of the tumor, for example precursor adenomas to metastatic adenocarcinoma. Generally, colorectal cancer can be treated by surgically removing the tumor, but overall survival rates remain between 45 and 60 percent. Colonic excision morbidity rates are fairly low and is generally associated with the anastomosis and not the extent of the removal of the tumor and local tissue. In patints with a high risk of reoccurrence, however, chemotherapy has been incorporated into the treatment regimen in order to improve survival rates.

Tumor metastasis prior to surgery is generally believed to be the cause of surgical intervention failure and up to one year of chemotherapy is required to kill the non-excised tumor cells. As severe toxicity is associated with the chemotherapeutic agents, only patients at high risk of recurrence are placed on chemotherapy following surgery.

Prostate Cancer

Prostate cancer is now the leading form of cancer among men and the second most frequent cause of death from cancer in men. It is estimated that more than 165,000 new cases of prostate cancer were diagnosed in 1993, and more than 35,000 men died from prostate cancer in that year. Additionally, the incidence of prostate cancer has increased by 50% since 1981, and mortality from this disease has continued to increase. Previously, most men died of other illnesses or diseases before dying from their prostate cancer. We now face increasing morbidity from prostate cancer as men live longer and the disease has the opportunity to progress.

Current therapies for prostate cancer focus upon reducing levels of dihydrotestosterone to decrease or prevent growth of prostate cancer. Radiation alone or in combination with surgery and/or chemotherapeutic agents is often used.

In addition to the use of digital rectal examination and transrectal ultrasonography, prostate-specific antigen (PSA) concentration is frequently used in the diagnosis of prostate cancer.

U.S. Pat. No. 4,472,382 discloses treatment of benign prostatic hyperplasia (BPH) with an antiandrogen and certain peptides which act as LH-RH agonists. U.S. Pat. No. 4,596,797 discloses aromatase inhibitors as a method of prophylaxis and/or treatment of prostatic hyperplasia. U.S. Pat. No. 4,760,053 describes a treatment of certain cancers which combines an LHRH agonist with an antiandrogen and/or an antiestrogen and/or at least one inhibitor of sex steroid biosynthesis. U.S. Pat. No. 4,775,660 discloses a method of treating breast cancer with a combination therapy which may include surgical or chemical prevention of ovarian secretions and administering an antiandrogen and an antiestrogen. U.S. Pat. No. 4,659,695 discloses a method of treatment of prostate cancer in susceptible male animals including humans whose testicular hormonal secretions are blocked by surgical or chemical means, e.g. by use of an LHRH agonist, which comprises administering an antiandrogen, e.g. flutamide, in association with at least one inhibitor of sex steroid biosynthesis, e.g. aminoglutethimide and/or ketoconazole.

Prostate Specific Antigen

One well known prostate cancer marker is Prostate Specific Antigen (PSA). PSA is a protein produced by prostate cells and is frequently present at elevated levels in the blood of men who have prostate cancer. PSA has been shown to correlate with tumor burden, serve as an indicator of metastatic involvement, and provide a parameter for following the response to surgery, irradiation, and androgen replacement therapy in prostate cancer patients. It should be noted that Prostate Specific Antigen (PSA) is a completely different protein from Prostate Specific Membrane Antigen (PSMA). The two proteins have different structures and functions and should not be confused because of their similar nomenclature.

Prostate Specific Membrane Antigen (PSMA)

In 1993, the molecular cloning of a prostate-specific membrane antigen (PSMA) was reported as a potential prostate carcinoma marker and hypothesized to serve as a target for imaging and cytotoxic treatment modalities for prostate cancer. Antibodies against PSMA have been described and examined clinically for diagnosis and treatment of prostate cancer. In particular, Indium-111 labeled PSMA antibodies have been described and examined for diagnosis of prostate cancer and indium-labeled PSMA antibodies have been described and examined for the treatment of prostate cancer.

Pancreas Cancer

Approximately 2% of new cancer cases diagnoses in the United States is pancreatic cancer. Pancreatic cancer is generally classified into two clinical types: 1) adenocarcinoma (metastatic and non-metastatic), and 2) cystic neoplasms (serous cystadenomas, mucinous cystic neoplasms, papilary cystic neoplasms, acinar cell systadenocarcinoma, cystic choriocarcinoma, cystic teratomas, angiomatous neoplasms).

Ovary Cancer

Celomic epithelial carcinoma accounts for approximately 90% of ovarian cancer cases. Preferred single agents that can be used in combination include: alkylating agents, ifosfamide, cisplatin, carboplatin, taxol, doxorubicin, 5-fluorouracil, methotrexate, mitomycin, hexamethylmelamine, progestins, antiestrogens, prednimustine, dihydroxybusulfan, galactitol, interferon alpha and interferon gamma.

Cancer of the fallopian tube is the least common type of ovarian cancer, accounting for approximately 400 new cancer cases per year in the United States. Papillary serous adenocarcinoma accounts for approximately 90% of all malignancies of the ovarian tube.

DETAILED DESCRIPTION OF THE INVENTION

Treatment of a neoplasia disorder in a mammal in need of such treatment is provided by methods and combinations using radiation and an integrin antagonist. The method comprises treating a mammal with a therapeutically effective amount of a combination comprising an integrin antagonist and a radiotherapeutic agent. Besides being useful for human treatment, the present invention is also useful for veterinary treatment of companion animals, exotic animals and farm animals, including mammals, rodents, and the like. More preferred animals include horses, dogs, and cats.

Integrin antagonist potentiate tumor response to radiation. Thus, integrin antagonists improve the efficacy of radiotherapy.

The methods and combinations of the present invention may be used for the treatment of neoplasia disorders selected from the group consisting of acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondrosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adenocarcinoma, pineal cell, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor.

The methods and compositions of the present invention provide one or more benefits. A combination of an integrin antagonist with radiation therapy of the present invention are useful in treating neoplasia disorders. Preferably, the integrin antagonist agent or agents and the radiation therapies of the present invention is administered in combination at a low dose, that is, at a dose lower than has been conventionally used in clinical situations for each of the individual components administered alone.

A benefit of lowering the dose of the radiation therapies of the present invention administered to a mammal includes a decrease in the incidence of adverse effects associated with higher dosages.

By lowering the incidence of adverse effects, an improvement in the quality of life of a patient undergoing treatment for cancer is contemplated. Further benefits of lowering the incidence of adverse effects include an improvement in patient compliance, and a reduction in the number of hospitalizations needed for the treatment of adverse effects.

Alternatively, the methods and combination of the present invention can also maximize the therapeutic effect at higher doses.

The phrase "combination therapy" (or "co-therapy") embraces the administration of a integrin antagonist and radiation therapy, and, optionally, an antineoplastic agent, as part of a specific treatment regimen intended to provide a beneficial effect from the co-action of the integrin antagonist and the radiation therapy. The beneficial effect of the combination includes, but is not limited to, pharmacokinetic or pharmacodynamic co-action resulting from the combination of the integrin antagonist and the radiation therapy. Administration of the integrin antagonist and the radiation therapy in combination typically is carried out over a defined time period (usually minutes, hours, days or weeks depending upon the combination selected). "Combination therapy" generally is not intended to encompass the administration of a integrin antagonist and radiation therapy as part of separate monotherapy regimens that incidentally and arbitrarily result in the combinations of the present invention. "Combination therapy" is intended to embrace administration of integrin antagonist and radiation therapy in a sequential manner, that is, wherein the integrin antagonist and the radiation therapy are administered at different times, as well as administration of the integrin antagonist and radiation therapy in a substantially simultaneous manner. Substantially simultaneous administration can be accomplished, for example, by administering to the subject concurrently with radiation therapy a single capsule having a fixed ratio of each therapeutic agent or in multiple, single capsules for each therapeutic agent. Sequential or substantially simultaneous administration of each therapeutic agent can be effected by any appropriate route including, but not limited to, oral routes, intravenous routes, intramuscular routes, and direct absorption through mucous membrane tissues. The therapeutic agents, if more than one, can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the integrin antagonist and radiation therapy are administered is not narrowly critical although radiation therapy typically will follow the administration of the integrin antagonist. "Combination therapy" also can embrace the administration of the integrin antagonist and radiation therapy as described above in further combination with other biologically active ingredients (such as, but not limited to, an antineoplastic agent) and non-drug therapies (such as, but not limited to, surgery). The radiation treatment of the combination may be conducted at any suitable time so long as a beneficial effect from the co-action of the combination of the integrin antagonist and radiation treatment is achieved. For example, in appropriate cases, the beneficial effect is still achieved even when the radiation treatment is temporally removed from the administration of the integrin antagonist, perhaps by days or even weeks.

The term "pharmaceutically acceptable" is used herein to mean that the modified noun is appropriate for use in a pharmaceutical product. Pharmaceutically acceptable cations include metallic ions and organic ions. More preferred metallic ions include, but are not limited to appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

Also included in the combination of the invention are the isomeric forms and tautomers of the described compounds and the pharmaceutically-acceptable salts thereof. Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric and galacturonic acids.

Suitable pharmaceutically-acceptable base addition salts of compounds of the present invention include metallic ion salts and organic ion salts. More preferred metallic ion salts include, but are not limited to appropriate alkali metal (group Ia) salts, alkaline earth metal (group Ia) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

An integrin antagonist of the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., Pharmaceutical Dosage Forms, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are solid at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, a contemplated aromatic sulfone hydroximate inhibitor compound can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated integrin antagonist compound can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

The term "treatment" refers to any process, action, application, therapy, or the like, wherein a mammal, including a human being, is subject to medical aid with the object of improving the mammal's condition, directly or indirectly.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention.

The term "prevention" includes either preventing the onset of clinically evident neoplasia altogether or preventing the onset of a preclinically evident stage of neoplasia in individuals at risk. Also intended to be encompassed by this definition is the prevention of initiation for malignant cells or to arrest or reverse the progression of premalignant cells to malignant cells. This includes prophylactic treatment of those at risk of developing the neoplasia.

Angiogenesis is an attractive therapeutic target because it is a multi-step process that occurs in a specific sequence, thus providing several possible targets for drug action. Examples of agents that interfere with several of these steps include specific integrin antagonists.

The phrase "therapeutically-effective" is intended to qualify the amount of each agent that will achieve the goal of improvement in neoplastic disease severity and the frequency of incidence over treatment of each agent by itself, while avoiding adverse side effects typically associated with alternative therapies.

A "therapeutic effect" relieves to some extent one or more of the symptoms of a neoplasia disorder. In reference to the treatment of a cancer, a therapeutic effect refers to one or more of the following: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anti-cancer agents.

"Therapeutic effective amount" is intended to qualify the amount required to achieve a therapeutic effect.

The phrases "low dose" or "low dose amount", in characterizing a therapeutically effective amount of the integrin antagonist and the radiation or therapy in the combination therapy, defines a quantity of such therapy, or a range of quantity of such therapy, that is capable of diminishing the neoplastic disease while reducing or avoiding one or more radiation-induced side effects, such as myelosupression, cardiac toxicity, skin erythema and desquamation, alopecia, inflammation or fibrosis.

The phrase "adjunctive therapy" includes agents such as those, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The phrase a "radiotherapeutic agent" refers to the use of electromagnetic or particulate radiation in the treatment of neoplasia. Examples of radiotherapeutic agents are provided in, but not limited to, radiation therapy and is known in the art (Hellman, Principles of Radiation Therapy, Cancer, in Principles and Practice of is Oncology, 248–75 (Devita et al., ed., 4 edit., volume 1, 1993).

The term "clinical tumor" includes neoplasms that are identifiable through clinical screening or diagnostic procedures including, but not limited to, palpation, biopsy, cell proliferation index, endoscopy, mammography, digital mammography, ultrasonography, computed tomography (CT), magnetic resonance imaging (MRI), positron emission tomography (PET), radiography, radionuclide evaluation, CT- or MRI-guided aspiration cytology, and imaging-guided needle biopsy, among others. Such diagnostic techniques are well known to those skilled in the art and are described in Cancer Medicine 4$^{th}$ Edition, Volume One. J. F. Holland, R. C. Bast, D. L. Morton, E. Frei III, D. W. Kufe, and R. R. Weichselbaum (Ed). Williams & Wilkins, Baltimore (1997).

The term "tumor marker" or "tumor biomarker" encompasses a wide variety of molecules with divergent haracteristics that appear in body fluids or tissue in association with a clinical tumor and also includes tumor-associated chromosomal changes. Tumor markers fall primarily into three categories: molecular or cellular markers, chromosomal markers, and serological or serum markers. Molecular and chromosomal markers complement standard parameters used to describe a tumor (i.e. histopathology, grade, tumor size) and are used primarily in refining disease diagnosis and prognosis after clinical manifestation. Serum markers can often be measured many months before clinical tumor detection and are thus useful as an early diagnostic test, in patient monitoring, and in therapy evaluation.

Molecular Tumor Markers

Molecular markers of cancer are products of cancer cells or molecular changes that take place in cells because of activation of cell division or inhibition of apoptosis. Expression of these markers can predict a cell's malignant potential. Because cellular markers are not secreted, tumor tissue samples are generally required for their detection. Non-limiting examples of molecular tumor markers that can be used in the present invention are listed in Table No. 1, below.

TABLE NO. 1

Non-limiting Examples of Molecular Tumor Markers

| Tumor | Marker |
| --- | --- |
| Breast | p53 |
| Breast, Ovarian | ErbB-2/Her-2 |
| Breast | S phase and ploidy |

TABLE NO. 1-continued

Non-limiting Examples of Molecular Tumor Markers

| Tumor | Marker |
| --- | --- |
| Breast | pS2 |
| Breast | MDR2 |
| Breast | urokinase plasminogen activator |
| Breast, Colon, Lung | myc family |

Chromosomal Tumor Markers

Somatic mutations and chromosomal aberrations have been associated with a variety of tumors. Since the identification of the Philadelphia Chromosome by Nowel and Hungerford, a wide effort to identify tumor-specific chromosomal alterations has ensued. Chromosomal cancer markers, like cellular markers, are can be used in the diagnosis and prognosis of cancer. In addition to the diagnostic and prognostic implications of chromosomal alterations, it is hypothesized that germ-line mutations can be used to predict the likelihood that a particular person will develop a given type of tumor. Non-limiting examples of chromosomal tumor markers that can be used in the present invention are listed in Table No. 2, below.

TABLE NO. 2

Non-limiting Examples of Chromosomal Tumor Markers

| Tumor | Marker |
| --- | --- |
| Breast | 1p36 loss |
| Breast | 6q24–27 loss |
| Breast | 11q22–23 loss |
| Breast | 11q13 amplification |
| Breast | TP53 mutation |
| Colon | Gain of chromosome 13 |
| Colon | Deletion of short arm of chromosome 1 |
| Lung | Loss of 3p |
| Lung | Loss of 13q |
| Lung | Loss of 17p |
| Lung | Loss of 9p |

Serological Tumor Markers

Serum markers including soluble antigens, enzymes and hormones comprise a third category of tumor markers. Monitoring serum tumor marker concentrations during therapy provides an early indication of tumor recurrence and of therapy efficacy. Serum markers are advantageous for patient surveillance compared to chromosomal and cellular markers because serum samples are more easily obtainable than tissue samples, and because serum assays can be performed serially and more rapidly. Serum tumor markers can be used to determine appropriate therapeutic doses within individual patients. For example, the efficacy of a combination regimen consisting of chemotherapeutic and antiangiogenic agents can be measured by monitoring the relevant serum cancer marker levels. Moreover, an efficacious therapy dose can be achieved by modulating the therapeutic-dose so as to keep the particular serum tumor marker concentration stable or within the reference range which may vary depending upon the indication. The amount of therapy can then be modulated specifically for each patient so as to minimize side effects while still maintaining stable, reference range tumor marker levels. Table No. 3 provides non-limiting examples of serological tumor markers that can be used in the present invention.

TABLE NO. 3

Non-limiting Examples of Serum Tumor Markers

| Cancer Type | Marker |
|---|---|
| Germ Cell Tumors | a-fetoprotein (AFP) |
| Germ Cell Tumors | human chorionic gonadotrophin (hCG) |
| Germ Cell Tumors | placental alkaline phosphatase (PLAP) |
| Germ Cell Tumors | lactate dehydrogenase (LDH) |
| Prostate | prostate specific antigen (PSA) |
| Breast | carcinoembryonic antigen (CEA) |
| Breast | MUC-1 antigen (CA15-3) |
| Breast | tissue polypeptide antigen (TPA) |
| Breast | tissue polypeptide specific antigen (TPS) |
| Breast | CYFRA 21.1 |
| Breast | soluble erb-B-2 |
| Ovarian | CA125 |
| Ovarian | OVX1 |
| Ovarian | cancer antigen CA72-4 |
| Ovarian | TPA |
| Ovarian | TPS |
| Gastrointestinal | CD44v6 |
| Gastrointestinal | CEA |
| Gastrointestinal | cancer antigen CA19-9 |
| Gastrointestinal | NCC-ST-439 antigen (Dukes C) |
| Gastrointestinal | cancer antigen CA242 |
| Gastrointestinal | soluble erb-B-2 |
| Gastrointestinal | cancer antigen CA195 |
| Gastrointestinal | TPA |
| Gastrointestinal | YKL-40 |
| Gastrointestinal | TPS |
| Esophageal | CYFRA 21-1 |
| Esophageal | TPA |
| Esophageal | TPS |
| Esophageal | cancer antigen CA19-9 |
| Gastric Cancer | CEA |
| Gastric Cancer | cancer antigen CA19-9 |
| Gastric Cancer | cancer antigen CA72-4 |
| Lung | neruon specific enolase (NSE) |
| Lung | CEA |
| \Lung | CYFRA 21-1 |
| Lung | cancer antigen CA 125 |
| Lung | TPA |
| Lung | squamous cell carcinoma antigen (SCC) |
| Pancreatic cancer | ca19-9 |
| Pancreatic cancer | ca50 |
| Pancreatic cancer | ca119 |
| Pancreatic cancer | ca125 |
| Pancreatic cancer | CEA |
| Pancreatic cancer | |
| Renal Cancer | CD44v6 |
| Renal Cancer | E-cadherin |
| Renal Cancer | PCNA (proliferating cell nuclear antigen) |

EXAMPLES

Germ Cell Cancers

Non-limiting examples of tumor markers useful in the present invention for the detection of germ cell cancers include, but are not limited to, a-fetoprotein (AFP), human chorionic gonadotrophin (hCG) and its beta subunit (hCGb), lactate dehydrogenase (LDH), and placental alkaline phosphatase (PLAP).

AFP has an upper reference limit of approximately ~10 kU/L after the first year of life and may be elevated in germ cell tumors, hepatocellular carcinoma and also in gastric, colon, biliary, pancreatic and lung cancers. AFP serum half life is approximately five days after orchidectomy. According to EGTM recommendations, AFP serum levels less than 1,000 kU/L correlate with a good prognosis, AFP levels between 1,000 and 10,000 kU/L, inclusive, correlate with intermediate prognosis, and AFP levels greater than 10,000 U/L correlate with a poor prognosis.

HCG is synthesized in the placenta and is also produced by malignant cells. Serum hCG concentrations may be increased in pancreatic adenocarcinomas, islet cell tumors, tumors of the small and large bowel, hepatoma, stomach, lung, ovaries, breast and kidney. Because some tumors only hCGb, measurement of both hCG and hCGb is recommended. Normally, serum hCG in men and pre-menopausal women is as high as ~5 U/L while post-menopausal women have levels up to ~10 U/L. Serum half life of hCG ranges from 16–24 hours. According to the EGTM, hCG serum levels under 5000 U/L correlate with a good prognosis, levels between 5000 and 50000 U/L, inclusively correlate with an intermediate prognosis, and hCG serum levels greater than 50000 U/L correlate with a poor prognosis. Further, normal hCG half lives correlate with good prognosis while prolonged half lives correlate with poor prognosis.

LDH is an enzyme expressed in cardiac and skeletal muscle as well as in other organs. The LDH-1 isoenzyme is most commonly found in testicular germ cell tumors but can also occur in a variety of benign conditions such as skeletal muscle disease and myocardial infarction. Total LDH is used to measure independent prognostic value in patients with advanced germ cell tumors. LDH levels less than 1.5× the reference range are associated with a good prognosis, levels between 1.5 and 10× the reference range, inclusive, are associated with an intermediate prognosis, and levels more than 10× the reference range are associated with a poor prognosis.

PLAP is a enzyme of alkaline phosphatase normally expressed by placental syncytiotrophoblasts. Elevated serum concentrations of PLAP are found in seminomas, non-seminomatous tumors, and ovarian tumors, and may also provide a marker for testicular tumors. PLAP has a normal half life after surgical resection of between 0.6 and 2.8 days.

Prostate Cancer

A nonlimiting example of a tumor marker useful in the present invention for the detection of prostate cancer is prostate specific antigen (PSA). PSA is a glycoprotein that is almost exclusively produced in the prostate. In human serum, uncomplexed f-PSA and a complex of f-PSA with a1-anthichymotrypsin make up total PSA (t-PSA). T-PSA is useful in determining prognosis in patients that are not currently undergoing anti-androgen treatment. Rising t-PSA levels via serial measurement indicate the presence of residual disease.

Breast Cancer

Non-limiting examples of serum tumor markers useful in the present invention for the detection of breast cancer include, but is not limited to carcinoembryonic antigen (CEA) and MUC-1 (CA 15.3). Serum CEA and CA15.3 levels are elevated in patients with node involvement compared to patients without node involvement, and in patients with larger tumors compared to smaller tumors. Normal range cutoff points (upper limit) are 5–10 mg/L for CEA and 35–60 u/ml for CA15.3. Additional specificity (99.3%) is gained by confirming serum levels with two serial increases of more than 15%.

Ovarian Cancer

A non-limiting example of a tumor marker useful in the present invention for the detection of ovarian cancer is CA125. Normally, women have serum CA125 levels between 0–35 kU/L; 99% of post-menopausal women have levels below 20 kU/L. Serum concentration of CA125 after chemotherapy is a strong predictor of outcome as elevated CA125 levels are found in roughly 80% of all patients with epithelial ovarian cancer. Further, prolonged CA125 half-life or a less than 7-fold decrease during early treatment is also a predictor of poor disease prognosis.

Gastrointestinal Cancers

A non-limiting example of a tumor marker useful in the present invention for the detection of colon cancer is carcinoembryonic antigen (CEA). CEA is a glycoprotein produced during embryonal and fetal development and has a high sensitivity for advanced carcinomas including those of the colon, breast, stomach and lung. High pre- or postoperative concentrations (>2.5 ng/ml) of CEA are associated with worse prognosis than are low concentrations. Further, some studies in the literature report that slow rising CEA levels indicates local recurrence while rapidly increasing levels suggests hepatic metastasis.

Lung Cancer

Examples of serum markers useful in the present invention to monitor lung cancer therapy include, but are not limited to, CEA, cytokeratin 19 fragments (CYFRA 21-1), and Neuron Specific Enolase (NSE).

NSE is a glycolytic isoenzyme of enolase produced in central and peripheral neurons and malignant tumors of neuroectodermal origin. At diagnosis, NSE concentrations greater than 25 ng/mL are suggestive of malignancy and lung cancer while concentrations greater than 100 ng/mL are suggestive of small cell lung cancer.

CYFRA 21-1 is a tumor marker test which uses two specific monoclonal antibodies against a cytokeratin 19 fragment. At diagnosis, CYFRA 21-1 concentrations greater than 10 ng/mL are suggestive of malignancy while concentrations greater than 30 ng/mL are suggestive of lung cancer.

Accordingly, dosing of the integrin antagonist and radiation therapy may be determined and adjusted based on measurement of tumor markers in body fluids or tissues, particularly based on tumor markers in serum. For example, a decrease in serum marker level relative to baseline serum marker prior to administration of the integrin antagonist and radiation therapy indicates a decrease in cancer-associated changes and provides a correlation with inhibition of the cancer. In one embodiment, therefore, the method of the present invention comprises administering the integrin antagonist and radiation therapy at doses that in combination result in a decrease in one or more tumor markers, particularly a decrease in one or more serum tumor markers, in the mammal relative to baseline tumor marker levels.

Similarly, decreasing tumor marker concentrations or serum half lives after administration of the combination indicates a good prognosis, while tumor marker concentrations which decline slowly and do not reach the normal reference range predict residual tumor and poor prognosis. Further, during follow-up therapy, increases in tumor marker concentration predicts recurrent disease many months before clinical manifestation.

In addition to the above examples, Table No. 4, below, lists several references, hereby individually incorporated by reference herein, that describe tumor markers and their use in detecting and monitoring tumor growth and progression.

TABLE NO. 4

Tumor marker references.

European Group on Tumor Markers Publications Committee. Consensus Recommendations. Anticancer Research 19: 2785–2820 (1999)
Human Cytogenetic Cancer Markers. Sandra R. Wolman and Stewart Sell (eds.). Totowa, New Jersey: Humana Press. 1997
Cellular Markers of Cancer. Carleton Garrett and Stewart Sell (eds.). Totowa, New Jersey: Human Press. 1995

The phrase "integrin antagonist" includes agents that impair endothelial cell adhesion via the various integrins. Integrin antagonists induce improperly proliferating endothelial cells to die, by interfering with molecules that blood vessel cells use to bridge between a parent blood vessel and a tumor.

Adhesion forces are critical for many normal physiological functions. Disruptions in these forces, through alterations in cell adhesion factors, are implicated in a variety of disorders, including cancer, stroke, osteoporosis, restenosis, and rheumatoid arthritis (A. F. Horwitz, *Scientific American*, 276:(5): 68–75, 1997).

Integrins are a large family of cell surface glycoproteins which mediate cell adhesion and play central roles in many adhesion phenomena. Integrins are heterodimers composed of noncovalently linked alpha and beta polypeptide subunits. Currently eleven different alpha subunits have been identified and six different beta subunits have been identified. The various alpha subunits can combine with various beta subunits to form distinct integrins.

One integrin known as $a_v b_3$ (or the vitronectin receptor) is normally associated with endothelial cells and smooth muscle cells. $A_v b_3$ integrins can promote the formation of blood vessels (angiogenesis) in tumors. These vessels nourish the tumors and provide access routes into the bloodstream for metastatic cells.

The $a_v b_3$ integrin is also known to play a role in various other disease states or conditions including tumor metastasis, solid tumor growth (neoplasia), osteoporosis, Paget's disease, humoral hypercalcemia of malignancy, angiogenesis, including tumor angiogenesis, retinopathy, arthritis, including rheumatoid arthritis, periodontal disease, psoriasis, and smooth muscle cell migration (e.g. restenosis).

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

The $a_v b_3$ integrin and a variety of other $a_v$-containing integrins bind to a number of Arg-Gly-Asp (RGD) containing matrix macromolecules. Compounds containing the RGD sequence mimic extracellular matrix ligands and bind to cell surface receptors. Fibronectin and vitronectin are among the major binding partners of $a_v b_3$ integrin. Other proteins and peptides also bind the $a_v b_3$ ligand. These include the disintegrins (M. Pfaff et al., *Cell Adhes. Commun.* 2(6): 491–501, 1994), peptides derived from phage display libraries (Healy, J. M. et al., *Protein Pept. Lett.* 3(1): 23–30, 1996; Hart, S. L. et al., *J. Biol. Chem.* 269(17): 12468–12474, 1994) and small cyclic RGD peptides (M. Pfaff et al., *J. Biol. Chem.*, 269(32): 20233–20238, 1994). The monoclonal antibody LM609 is also an $a_v b_3$ integrin antagonist (D. A. Cheresh et al., *J. Biol. Chem.*, 262(36): 17703–17711, 1987).

$A_vb_3$ inhibitors are being developed as potential anticancer agents. Compounds that impair endothelial cell adhesion via the $a_vb_3$ integrin induce improperly proliferating endothelial cells to die.

The $a_vb_3$ integrin has been shown to play a role in melanoma cell invasion (Seftor et al., *Proc. Natl. Acad. Sci. USA*, 89: 1557–1561, 1992). The $a_vb_3$ integrin expressed on human melanoma cells has also been shown to promote a survival signal, protecting the cells from apoptosis (Montgomery et al., *Proc. Natl. Acad. Sci. USA*, 91: 8856–8860, 1994).

Mediation of the tumor cell metastatic pathway by interference with the $a_vb_3$ integrin cell adhesion receptor to impede tumor metastasis would be beneficial. Antagonists of $a_vb_3$ have been shown to provide a therapeutic approach for the treatment of neoplasia (inhibition of solid tumor growth) because systemic administration of $a_vb_3$ antagonists causes dramatic regression of various histologically distinct human tumors (Brooks et al., *Cell*, 79: 1157–1164, 1994).

The adhesion receptor identified as integrin a $b_3$ is a marker of angiogenic blood vessels in chick and man. This receptor plays a critical role in angiogenesis or neovascularization. Angiogenesis is characterized by the invasion, migration and proliferation of smooth muscle and endothelial cells by new blood vessels. Antagonists of $a_vb_3$ inhibit this process by selectively promoting apoptosis of cells in the neovasculature. The growth of new blood vessels, also contributes to pathological conditions such as diabetic retinopathy (Adonis et al., *Amer. J. Ophthal.*, 118: 445–450, 1994) and rheumatoid arthritis (Peacock et al., *J. Exp. Med.*, 175:, 1135–1138, 1992). Therefore, $a_vb_3$ antagonists can be useful therapeutic targets for treating such conditions associated with neovascularization (Brooks et al., *Science*, 264: 569–571, 1994).

The $a_vb_3$ cell surface receptor is also the major integrin on osteoclasts responsible for the attachment to the matrix of bone. Osteoclasts cause bone resorption and when such bone resorbing activity exceeds bone forming activity, osteoporosis (a loss of bone) results, which leads to an increased number of bone fractures, incapacitation and increased mortality. Antagonists of $a_vb_3$ have been shown to be potent inhibitors of osteoclastic activity both in vitro (Sato et al., *J. Cell. Biol.*, 111: 1713–1723, 1990) and in vivo (Fisher et al., *Endocrinology*, 132: 1411–1413, 1993). Antagonism of $a_vb_3$ leads to decreased bone resorption and therefore assists in restoring a normal balance of bone forming and resorbing activity. Thus it would be beneficial to provide antagonists of osteoclast $a_vb_3$ which are effective inhibitors of bone resorption and therefore are useful in the treatment or prevention of osteoporosis.

PCT int. Appl. WO 97/08145 by Sikorski et al., discloses meta-guanidine, urea, thiourea or azacyclic amino benzoic acid derivatives as highly specific $a_vb_3$ integrin antagonists.

PCT Int. Appl. WO 96/00574 A1 960111 by Cousins, R. D. et. al., describe preparation of 3-oxo-2,3,4,5-tetrahydro-1H-1,4-benzodiazepine and -2-benzazepine derivatives and analogs as vitronectin receptor antagonists.

PCT Int. Appl. WO 97/23480 A1 970703 by Jadhav, P. K. et. al. describe annelated pyrazoles as novel integrin receptor antagonists. Novel heterocycles including 3-[1-[3-(imidazolin-2-ylamino)propyl]indazol-5-ylcarbonylamino]-2-(benzyl oxycarbonylamino)propionic acid, which are useful as antagonists of the $a_vb_3$ integrin and related cell surface adhesive protein receptors.

PCT Int. Appl. WO 97/26250 A1 970724 by Hartman, G. D. et al., describe the preparation of arginine dipeptide mimics as integrin receptor antagonists. Selected compounds were shown to bind to human integrin $a_vb_3$ with EIB <1000 nM and claimed as compounds, useful for inhibiting the binding of fibrinogen to blood platelets and for inhibiting the aggregation of blood platelets.

PCT Int. Appl. WO 97/23451 by Diefenbach, B. et. al. describe a series of tyrosine-derivatives used as alpha v-integrin inhibitors for treating tumors, osteoporosis, osteolytic disorder and for suppressing angiogenesis.

PCT Int. Appl. WO 96/16983 A1 960606. by Vuori, K. and Ruoslahti, E. describe cooperative combinations of $a_vb_3$ integrin ligand and second ligand contained within a matrix, and use in wound healing and tissue regeneration. The compounds contain a ligand for the $a_vb_3$ integrin and a ligand for the insulin receptor, the PDGF receptor, the IL-4 receptor, or the IGF receptor, combined in a biodegradable polymeric (e.g. hyaluronic acid) matrix.

PCT Int. Appl. WO 97/10507 A1 970320 by Ruoslahti, E; and Pasqualini, R. describe peptides that home to a selected organ or tissue in vivo, and methods of identifying them. A brain-homing peptide, nine amino acid residues long, for example, directs red blood cells to the brain. Also described is use of in vivo panning to identify peptides homing to a breast tumor or a melanoma.

PCT Int. Appl. WO 96/01653 A1 960125 by Thorpe, Philip E.; Edgington, Thomas S. describes bifunctional ligands for specific tumor inhibition by blood coagulation in tumor vasculature. The disclosed bispecific binding ligands bind through a first binding region to a disease-related target cell, e.g. a tumor cell or tumor vasculature; the second region has coagulation-promoting activity or is a binding region for a coagulation factor. The disclosed bispecific binding ligand may be a bispecific (monoclonal) antibody, or the two ligands may be connected by a (selectively cleavable) covalent bond, a chemical linking agent, an avidin-biotin linkage, and the like. The target of the first binding region can be a cytokine-inducible component, and the cytokine can be released in response to a leukocyte-activating antibody; this may be a bispecific antibody which crosslinks activated leukocytes with tumor cells.

Nonlimiting examples of integrin antagonists that may be used in the present invention are identified in Table 5, below.

TABLE NO. 5

Examples of Integrin antagonists

| Compound | Trade/ Research Name | Mode of Action | Reference | Dosage |
|---|---|---|---|---|
| 2(S)-Benzenesulfon-amido)-3-[4-[2-(3,4,5,6-tetrahydropyrimidin-2-ylamino)ethoxy]benzamido]propionic acid | L-748415 | Vitronectin antagonist | | |
| | Merk KGaA Compound 125 | | | |
| Ethyl beta-[[2-[[[3-[(3,4,5,6,-tetrahydro-2H-azepin-7-yl)amino]phenyl]carbonyl]amino]acetyl]-amino]pyridine-3-propanoic acid | | Vitronectin antagonist | WO 97/08145 | |

TABLE NO. 5-continued

Examples of Integrin antagonists

| Compound | Trade/Research Name | Mode of Action | Reference | Dosage |
|---|---|---|---|---|
| O-[9,10-dimethoxy-1,2,3,4,5,6-hexahydro-4-[(1,4,5,6-tetrahydro-2-pyrimidinyl)hydrazono]-8-benz(e)azulenyl]-N-[(phenylmethoxy)carbonyl]-DL-homoserine 2,3-dihydroxypropyl ester | | Vitronectin antagonist | WO 97/34865 | |
| (2S)-Benzoylcarbonyl amino-3-[2-((4S)-(3-(4,5-dihydro-1H-imidazol-2-ylamino)-propyl)-2,5-dioxo-imidazolidin-1-yl)-acetylamino]-propionate | | Vitronectin antagonist | EP 796855 | |
| | S-836 | Vitronectin antagonist; Angiogenesis inhibitor; solid tumors | | |
| (S)-2-[7-[N-(Benzimidazol-2-ylmethyl)-N-methylcarbamoyl]-4-methyl-3-oxo-2,3,4,5-tetrahydro-1H-1,4-benzodiazepin-2-yl]acetic acid | SB-223245 | Vitronectin antagonist; Angiogenesis inhibitor | | |
| | SD-983 | Vitronectin antagonist; Angiogenesis inhibitor | | |
| Isoxaoline derivatives | | Vitronectin receptor antagonist | WO 96/37492 | 0.001–10 mg/kg/day; 0.01–0.5 (pref. 0.01–0.1) mg/kg/day intranasally |
| (2S)-Bensoylcarbonyl amino-3-[2-((4S)-(3-(4,5-dihydro-1H-imidazol-2-ylamino)-propyl)-2,5-dioxo-imidazolindin-1-yl)-acetylamino]-propionate | | Vitronectin antagonist | EP 796855 | |
| Benzazulene deriviatives; O-[9,10-dimethoxy-1,2,3,4,5,6-hexahydro-4-[(1,4,5,6-tetrahydro-2-pyrimidinyl)hydrazono]-8-benz(e)azzulenyl]-N-[(phenylmethoxy)carbonyl]-DL-homoserine 2,3-dihydroxypropyl ester | | Vitronectin antagonist | WO 97/34865 | |
| Immunoglobulin G, (human-mouse monoclonal c7E3 clone p7E3VHhC gamma 4 Fab fragment anti-human glycoprotein IIb/IIIa receptor), disulfide with human-mouse monoclonal c7E3 clone p7E3VkhCk light chain-Arg-Gly-Asp-phe-Val | abciximab; ReoPro | GPIIb IIIa receptor antagonist; Vitronectin antagonist | | Recomended dosage: Intravenous bolus of 0.25 mg/kg, followed by 10 µ/min for 12 hrs. |
| | cRGDfV pentapeptide | Apoptosis agonist; Vitronectin antagonist | | |
| | vitronectin antagonist | Vitronectin antagonist | | Orally active |

Further examples of integrin antagonists can be found in the following documents:

| | | | |
|---|---|---|---|
| WO 98/07432 | WO 98/16227 | WO 97/36862 | WO 97/36861 |
| WO 97/36860 | WO 9736859 | WO 97/36858 | US 5639765 |
| WO 97/08145 | US 5639765 | WO 98/22500 | WO 98/20897 |
| WO 98/18764 | WO 98/14192 | WO 98/08840 | WO 98/04913 |
| WO 97/48395 | WO 9744333 | WO 98/00395 | WO 97/41102 |
| WO 97/34865 | WO 97/39028 | WO 97/37655 | WO 97/33887 |
| EP 796855 | WO 97/26250 | WO 97/24124 | WO 97/24122 |
| WO 97/24336 | WO 97/24119 | WO 97/23480 | WO 97/23451 |
| EP 765660 | WO 97/14716 | EP 77/1818 | WO 97/01540 |
| WO 96/37492 | EP 741133 | US 5565449 | WO 96/26190 |
| EP 727425 | US 5627197 | DE 4439846 | EP 711770 |
| EP 710657 | WO 96/06087 | WO 96/00730 | WO 96/00574 |
| WO 95/23811 | US 5464855 | WO 95/28426 | JP 07242645 |
| JP 07206860 | EP 645376 | WO 95/07712 | WO 95/00544 |
| AU 9464771 | EP 614664 | WO 94/21607 | WO 94/15936 |
| JP 06128289 | WO 9411739 | WO 93/08174 | EP 537654 |
| EP 529858 | US 5229366 | WO 92/07870 | WO 92/00995 |
| EP 381033 | WO 98/08518 | US 5721210 | EP 820991 |
| EP 820988 | WO 97/48444 | WO 97/41844 | WO 97/45447 |
| WO 97/45137 | US 5686570 | US 5686568 | US 5686571 |
| US 5686569 | US 5686567 | US 5686566 | WO 97/41149 |
| DE 19613933 | WO 97/35615 | WO 97/25031 | US 5639726 |
| WO 97/18838 | WO 97/11718 | US 5612311 | EP 77/0622 |
| WO 97/08203 | WO 9706791 | WO 97/03094 | WO 96/40781 |
| WO 96/40250 | US 5536814 | US 5510332 | WO 96/07734 |
| WO 96/05304 | WO 96/00581 | WO 95/34641 | WO 95/30438 |

-continued

| | | | |
|---|---|---|---|
| DE 4415310 | EP 668278 | EP 656348 | DE 4336758 |
| EP 623615 | DE 4310643 | AU 9459185 | WO 94/01152 |
| CA 2120303 | EP 632053 | EP 618225 | WO 94/18981 |
| WO 94/13310 | JP 06116289 | WO 94/05310 | EP 58/9181 |
| EP 589181 | US 5491129 | WO 93/25218 | WO 93/20229 |
| US 5225531 | EP 570352 | EP 570352 | WO 92/09200 |
| WO 91/15515 | EP 445796 | WO 91/07977 | EP 410767 |
| US 5061693 | EP 384362 | US 5663297 | EP 372486 |
| US 5039805 | WO 9003983 | WO 89/05155 | DE 19548798 |
| DE 19626701 | DE 19653645 | DE 9653646 | DE 19653647 |
| DE 19654483 | DE 4439846 | EP 683173 | EP 537654 |
| EP 645376 | EP 0710657 | EP 727425 | EP 741133 |
| EP 771565 | EP 0846702 | EP 853084 | JP 07285992 |
| JP 08337523 | JP 09169742 | JP 9235239 | JP 09316000 |
| JP 10045587 | JP 08183752 | JP 183788 | US 5574026 |
| WO 95/14714 | WO 9525543 | WO 95/28426 | WO 95/32710 |
| WP 96/06087 | WO 96/26190 | WO 96/32945 | WO 97/12625 |
| WO 97/15666 | WO 97/16197 | WO 97/21726 | WO 97/22596 |
| WO 97/23625 | WO 97/24336 | WO 98/25892 | WO 98/25601 |
| WO 97/26258 | WO 97/33576 | WO 98/00144 | WO 98/00395 |
| WO 98/03573 | WO 98/08518 | WO 98/08840 | WO 98/10795 |
| WO 98/11089 | WO 98/11223 | WO 98/12226 | WO 98/13071 |
| WO 98/13350 | WO 98/13354 | WO 98/14192 | WO 98/15278 |
| WO 98/15574 | WO 98/18460 | WO 98/18461 | WO 98/18764 |
| WO 98/21230 | WO 98/23608 | WO 98/23613 | |

The following individual references each hereby incorporated by reference herein, describe various integrin antagonists suitable for use in the invention described herein, and processes for their manufacture:

| | | | |
|---|---|---|---|
| WO 98/07432 | WO 98/16227 | WO 97/36862 | WO 97/36861 |
| WO 97/36860 | WO 97/36859 | WO 97/36858 | US 5639765 |
| WO 97/08145 | US 5639765 | WO 98/22500 | WO 98/20897 |
| WO 98/18764 | WO 98/14192 | WO 98/08840 | WO 98/04913 |
| WO 97/48395 | WO 97/44333 | WO 98/00395 | WO 97/41102 |
| WO 97/34865 | WO 97/39028 | WO 97/37655 | WO 97/33887 |
| EP 79/6855 | WO 97/26250 | WO 97/24124 | WO 97/24122 |
| WO 97/24336 | WO 97/24119 | WO 97/23480 | WO 97/23451 |
| EP 76/5660 | WO 97/14716 | EP 771818 | WO 97/01540 |
| WO 96/37492 | EP 74/1133 | US 5565449 | WO 96/26190 |
| EP 72/7425 | US 5627197 | DE 4439846 | EP 711770 |
| EP 71/0657 | WO 96/06087 | WO 96/00730 | WO 96/00574 |
| WO 95/23811 | US 5464855 | WO 95/28426 | JP 07242645 |
| JP 07/206860 | EP 64/5376 | WO 95/07712 | WO 95/00544 |
| AU 94/64771 | EP 61/4664 | WO 94/21607 | WO 94/15936 |
| JP 06/128289 | WO 94/11739 | WO 93/08174 | EP 537654 |
| EP 52/9858 | US 52/29366 | WO 92/07870 | WO 92/00995 |
| EP 38/1033 | WO 98/08518 | US 572,210 | EP 820991 |
| EP 82/0988 | WO 97/48444 | WO 97/41844 | WO 97/45447 |
| WO 97/45137 | US 5686570 | US 5686568 | US 5686571 |
| US 5686569 | US 5686567 | US 5686566 | WO 97/41149 |
| DE 19/613933 | WO 97/35615 | WO 97/25031 | US 5639726 |
| WO 97/18838 | WO 97/11718 | US 5612311 | EP 770622 |
| WO 97/08203 | WO 97/06791 | WO 97/03094 | WO 96/40781 |
| WO 96/40250 | WO 95/36814 | US 5510332 | WO 96/07734 |
| WO 96/05304 | WO 96/00581 | WO 95/34641 | WO 95/30438 |
| DE 44/15310 | EP 66/8278 | EP 656348 | DE 4336758 |
| EP 62/3615 | DE 43/10643 | AU 94/59185 | NO 94/01152 |
| CA 21/20303 | EP 63/2053 | EP 618225 | WO 94/18981 |
| WO 94/13310 | JP 06/116289 | WO 94/05310 | EP 58/9181 |
| EP 58/9181 | US 5491129 | WO 93/25218 | WO 93/20229 |
| U.S. 5225531 | EP 570352 | EP 57/0352 | WO 92/09200 |
| WO 91/15515 | EP 445796 | WO 91/07977 | EP 410767 |
| US 5061693 | EP 384362 | US 5,63297 | EP 37/2486 |
| US 5039805 | WO 90/03983 | WO 89/05155 | DE 19548798 |
| DE 19/626701 | DE 19653645 | DE 19653646 | DE 19653647 |
| DE 19/654483 | DE 4439846 | EP 683173 | EP 537654 |
| EP 0/645376 | EP 0710657 | EP 727425 | EP 741133 |
| EP 0/771565 | EP 0846702 | EP 853084 | JP 07285992 |
| JP 08/337523 | JP 09169742 | JP 09235239 | JP 09316000 |
| JP 10/045587 | JP 08183752 | JP 08183788 | US 5574026 |
| WO 95/14714 | WO 95/25543 | WO 95/28426 | WO 95/32710 |
| WP 96/06087 | WO 96/26190 | WO 96/32945 | WO 97/12625 |
| WO 97/15666 | WO 97/16197 | WO 97/21726 | WO 97/22596 |
| WO 97/23625 | WO 97/24336 | WO 98/25892 | WO 98/25601 |
| WO 97/26258 | WO 97/33576 | WO 98/00144 | WO 98/00395 |
| WO 98/03573 | WO 98/08518 | WO 98/08840 | WO 98/10795 |
| WO 98/11089 | WO 98/11223 | WO 98/12226 | WO 98/13071 |
| WO 98/13350 | WO 98/13354 | WO 98/14192 | WO 98/15278 |
| WO 98/15574 | WO 98/18460 | WO 98/18461 | WO 98/18764 |
| WO 98/21230 | WO 98/23608 | WO 98/23613 | |

The following individual references each hereby incorporated by reference herein, describe additional integrin antagonists suitable for use in the invention described herein, and processes for their manufacture:

| | | | |
|---|---|---|---|
| WO 99/50249 | WO 99/45927 | WO 99/44994 | US 5955572 |
| US 59552341 | WO 99/38849 | WO 99/37683 | WO 99/37621 |
| WO 99/33798 | EP 928793 | US 5925655 | US 5919792 |
| WO 99/32457 | WO 99/31099 | US 5912234 | WO 99/31061 |
| WO 99/31061 | WO 99/30713 | WO 99/30709 | WO 99/26945 |
| WO 99/15508 | WO 99/15507 | WO 99/15506 | WO 99/15178 |
| WO 99/15170 | WO 99/11626 | WO 99/06049 | WO 99/05107 |
| US 5852210 | US 5843906 | WO 98/54217 | US 5840961 |
| WO 98/43962 | US 5773646 | US 5773644 | WO 98/33919 |
| WO 98/31359 | WO 98/30542 | EP 854145 | EP 854140 |
| EP 853084 | US 5773412 | US 5766591 | US 5760028 |
| US 5759996 | WO 98/15278 | US 5741796 | WO 98/10795 |
| WO 97/08145 | | | |

The Vitaxin used in the therapeutic combinations of the present invention can be prepared in the manner set forth in WO 98/33,919.

Some Preferred integrin antagonists that may be used in the present invention are listed in the following references hereby each individually incorporated by reference, herein: U.S. Pat. No. 5,773,644; U.S. Pat. No. 5,773,646; patent application Ser. No. U.S. 092/89,140; U.S. Pat. No. 5,852,210; U.S. Pat. No. 5,843,906; U.S. patent application Ser. No. 091/41,547; U.S. Pat. No. 5,952,381; U.S. patent application Ser. No. 092/88,742; patent application Ser. No. U.S. 600/03,277; patent application Ser. No. U.S. 087/13,555; patent application Ser. No. U.S. 092/15,229; patent application Ser. No. U.S. 090/34,758; patent application Ser. No. U.S. 092/61,822; WO 98/33919.

More preferred integrin antagonists that may be used in the present invention include, but are not limited to

I1)

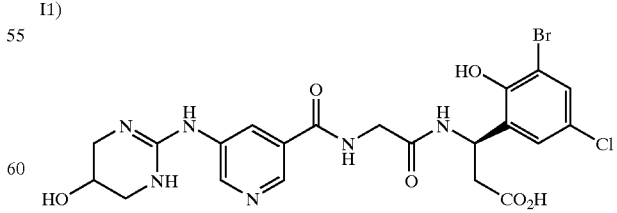

(3R)-N-[[5-[(1,4,5,6-tetrahydro-5-hydroxy-2-pyrimidinyl)amino]-3-pyridinyl]carbonyl]glycyl-3-(3-bromo-5-chloro-2-hydroxyphenyl)-b-alanine;

I2)

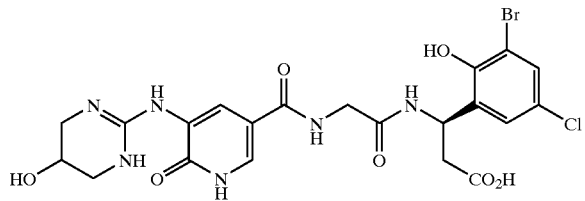

(3R)-N-[[1,6-dihydro-6-oxo-5-[(1,4,5,6-tetrahydro-5-hydroxy-2-pyrimidinyl)amino]-3-pyridinyl]carbonyl]glycyl-3-(3-bromo-5-chloro-2-hydroxyphenyl)-b-alanine;

I3)

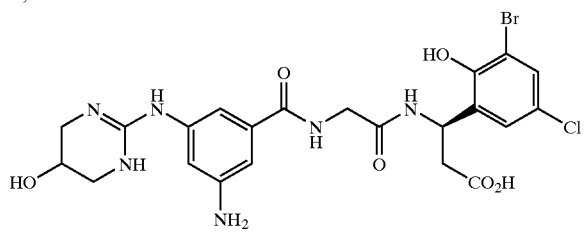

(3R)-N-[3-amino-5-[(1,4,5,6-tetrahydro-5-hydroxy-2-pyrimidinyl)amino]benzoyl)glycyl-3-(3-bromo-5-chloro-2-hydroxyphenyl)-b-alanine;

I4)

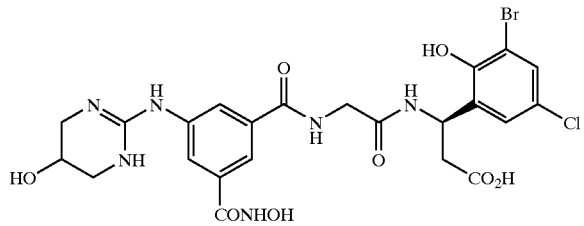

(3R)-N-[3-[(hydroxyamino)carbonyl]-5-[(1,4,5,6-tetrahydro-5-hydroxy)-2-pyrimidinyl)amino]benzoyl]glycyl-3-(3-bromo-5-chloro-2-hydroxyphenyl)-b-alanine;

I5)

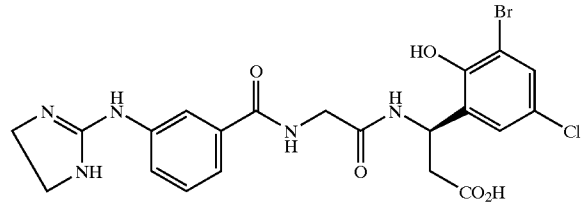

(3R)-N-[3-[(4-,5-dihydro-1H-imidazol-2-yl)amino]benzoyl]glycyl-3-(3-bromo-5-chloro-2-hydroxyphenyl)-b-alanine;

I6)

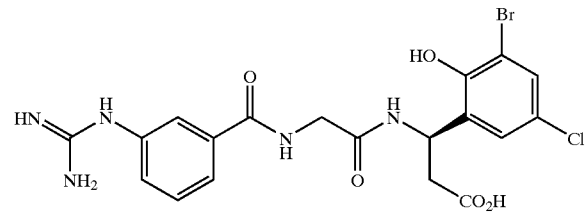

(3R)-N-[3-[(aminoiminomethyl)amino]benzoyl]glycyl-3-(3-bromo-5-chloro-2-hydroxyphenyl)-b-alanine;

I7)

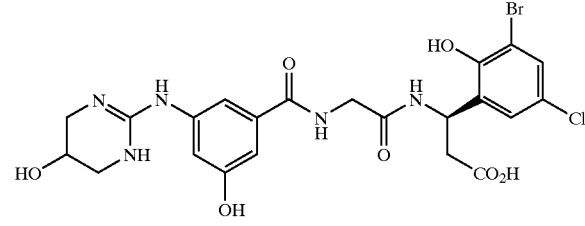

(3R)-N-[3-hydroxy-5-[(1,4,5,6-tetrahydro-5-hydroxy-2-pyrimidinyl)amino]benzoyl]glycyl-3-(3-bromo-5-chloro-2-hydroxyphenyl)-b-alanine;

I8)

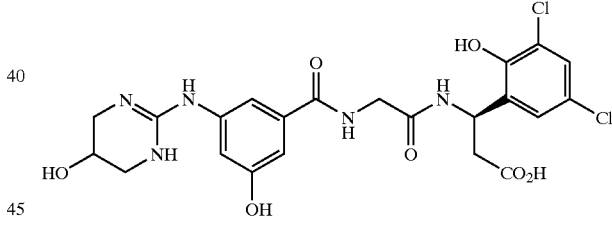

(3R)-N-[3-hydroxy-5-[(1,4,5,6-tetrahydro-5-hydroxy-2-pyrimidinyl)amino]benzoyl]glycyl-3-(3,5-dichloro-2-hydroxyphenyl)-b-alanine;

I9)

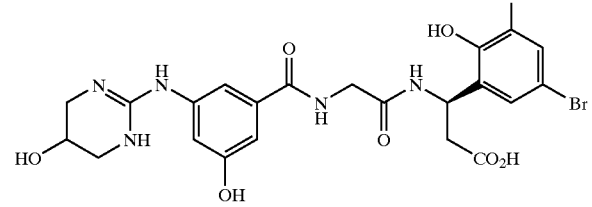

(3R)-N-[3-hydroxy-5-[(1,4,5,6-tetrahydro-5-hydroxy-2-pyrimidinyl)amino]benzoyl]glycyl-3-(5-bromo-3-chloro-2-hydroxyphenyl)-b-alanine;

I10)

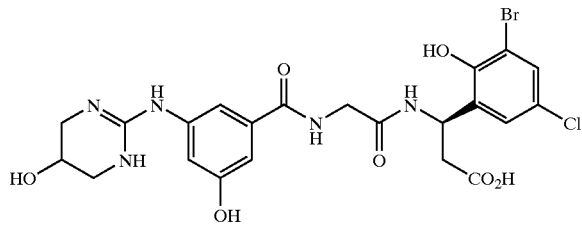

(3R)-N-[3-hydroxy-5-[(1,4,5,6-tetrahydro-5-hydroxy-2-pyrimidinyl)amino]benzoyl]glycyl-3-(3-bromo-5-chloro-2-hydroxyphenyl)-b-alanine;

I11)

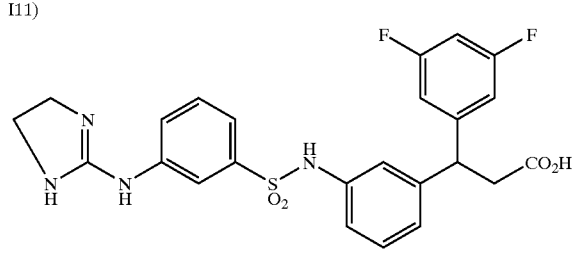

b-[3-[[(3-[[4,5-dihydro-1H-imidazol-2-yl)amino]phenyl]sulfonyl]amino]phenyl]-3,5-difluorobenzenepropanoic acid;

I12)

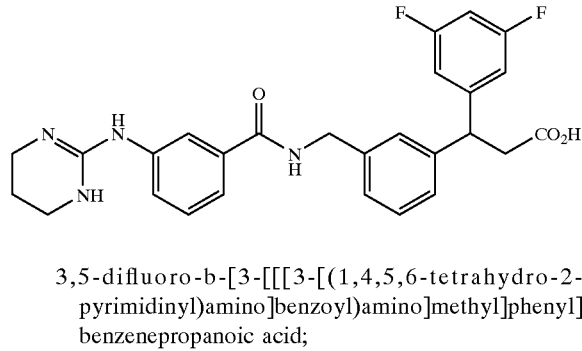

3,5-difluoro-b-[3-[[[3-[(1,4,5,6-tetrahydro-2-pyrimidinyl)amino]benzoyl)amino]methyl]phenyl]benzenepropanoic acid;

I13)

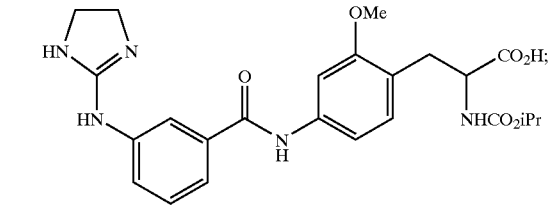

I14)

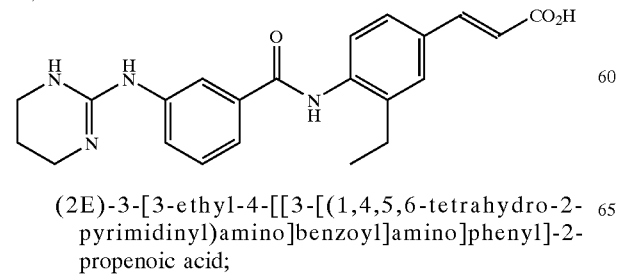

(2E)-3-[3-ethyl-4-[[3-[(1,4,5,6-tetrahydro-2-pyrimidinyl)amino]benzoyl]amino]phenyl]-2-propenoic acid;

I15)

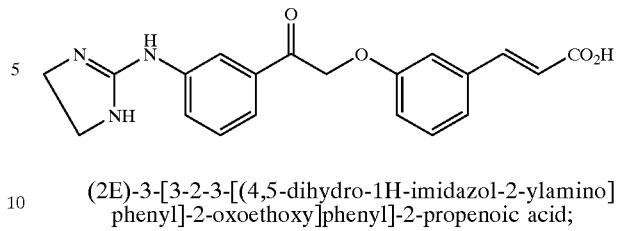

(2E)-3-[3-2-3-[(4,5-dihydro-1H-imidazol-2-ylamino]phenyl]-2-oxoethoxy]phenyl]-2-propenoic acid;

I16)

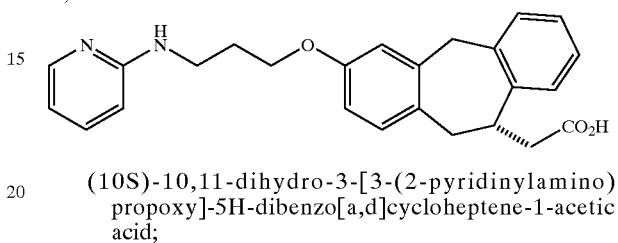

(10S)-10,11-dihydro-3-[3-(2-pyridinylamino)propoxy]-5H-dibenzo[a,d]cycloheptene-1-acetic acid;

I17)

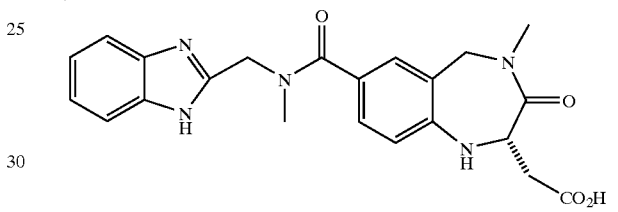

(2S)-7-[[(1H-benzimidazol-2-ylmethyl)methylamino]carbonyl]-2,3,4,5-tetrahydro-4-methyl-3-oxo-1H-1,4-benzodiazepine-2-acetic acid;

I18)

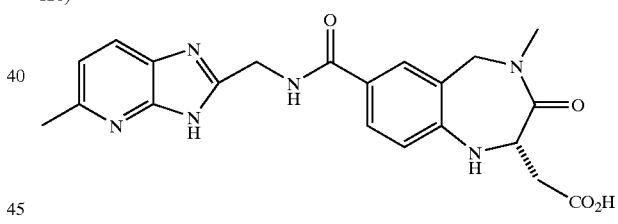

(2S)-2,3,4,5-tetrahydro-4-methyl-7-[[[(5-methyl-1H-imidazo[4,5-b]pyridin-2-yl]methyl]amino]carbonyl]-3-oxo-1H-1,4-benzodiazepine-2-acetic acid;

I19)

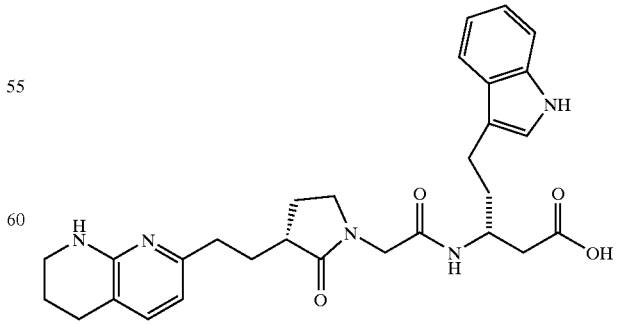

(bR)-b-[[[(3R)-2-oxo-3-[2-(1,5,6,7-tetrahydro-1,8-naphthyridin-2-yl)ethyl]-1-pyrrolidinyl]acetyllamino]-1H-indole-3-pentanoic acid;

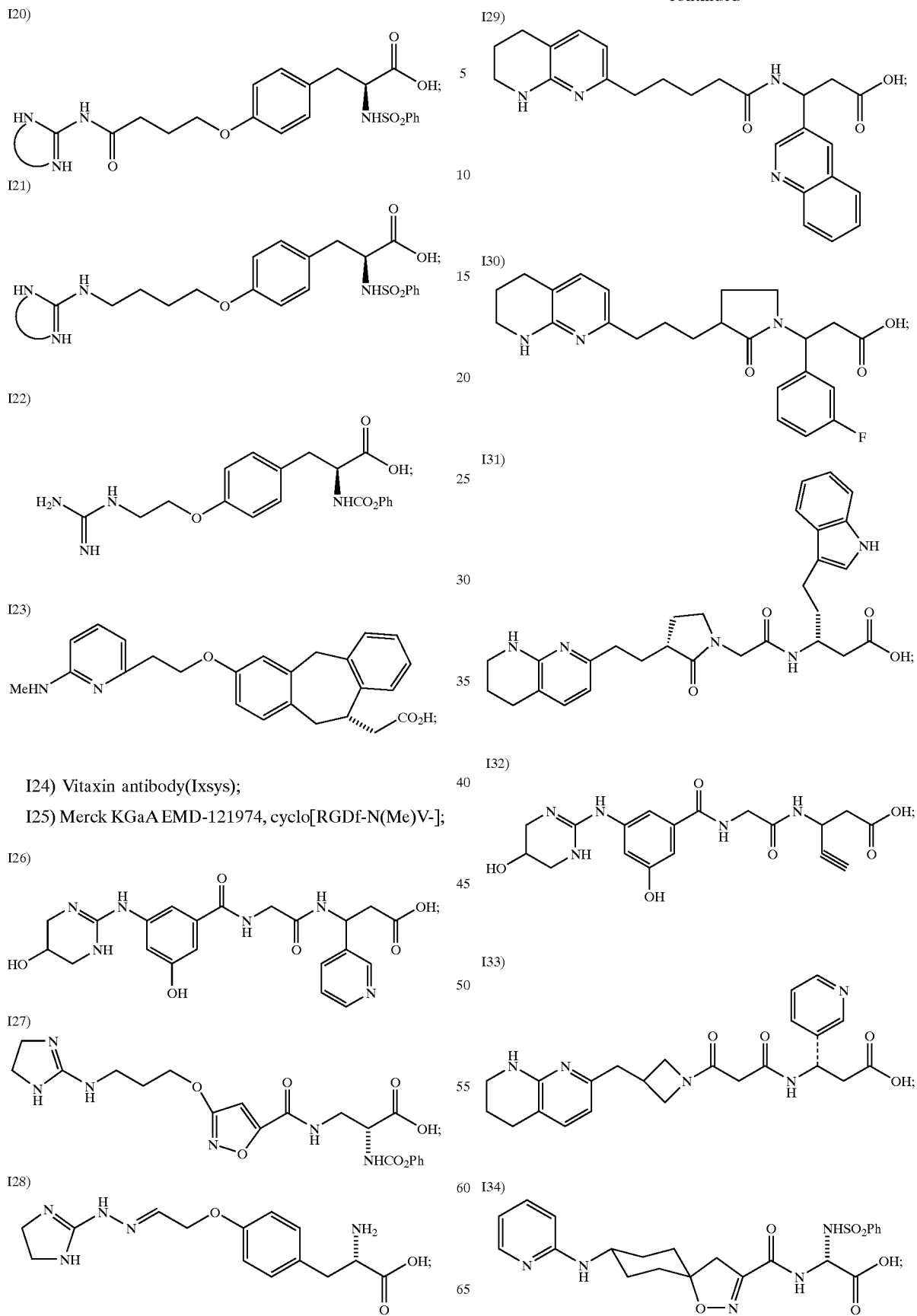
I24) Vitaxin antibody(Ixsys);
I25) Merck KGaA EMD-121974, cyclo[RGDf-N(Me)V-];

I35) 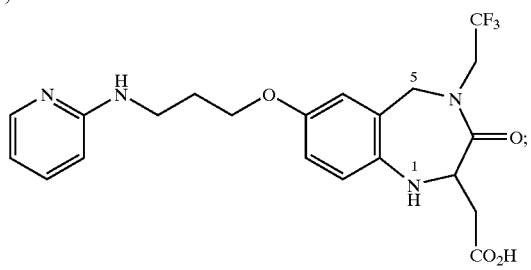

I36) 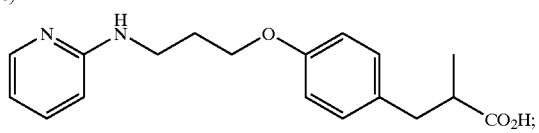

I37) 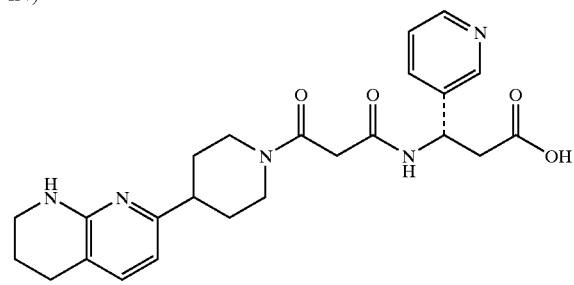

I38) 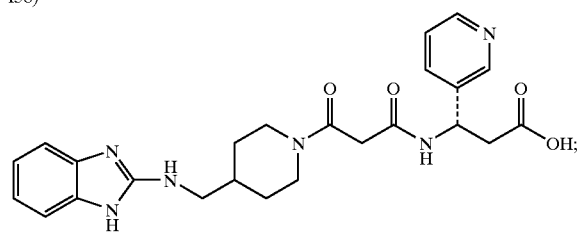

I39) 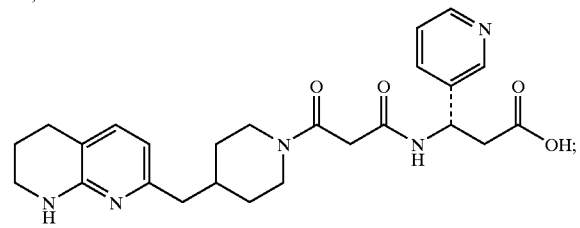

I40) 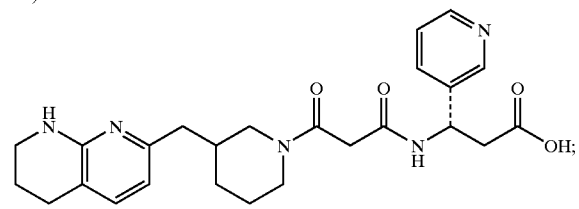

I41) 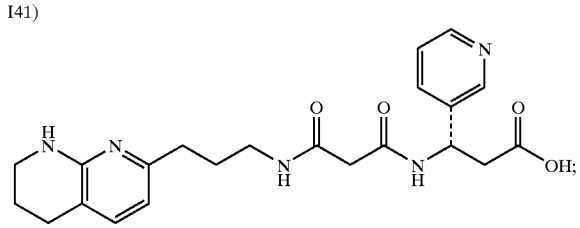

I42) 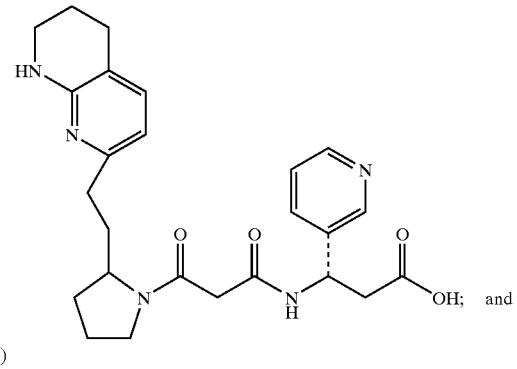

and

I43) 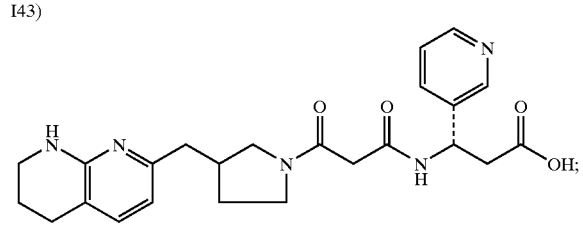

Still more preferred integrin antagonists include but are not limited to

I16) 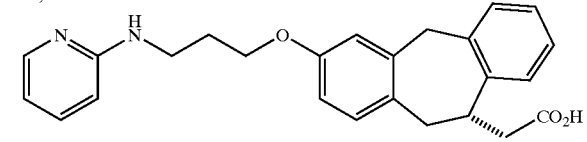

(10S)-10,11-dihydro-3-[3-(2-pyridinylamino)propoxyl-5H-dibenzo(a,d)cycloheptene-10-acetic acid;

I17) 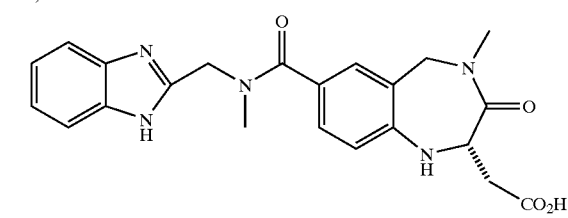

(2S)-7-[[(1H-benzimidazol-2-ylmethyl)methylamino]carbonyl]-2,3,4,5-tetrahydro-4-methyl-3-oxo-1H-1,4-benzodiazepine-2-acetic acid;

I18) 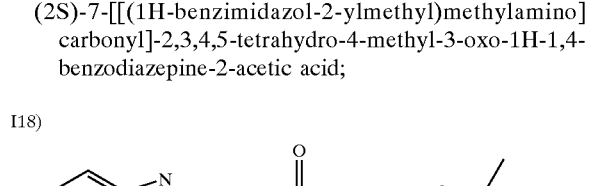

(2S)-2,3,4,5-tetrahydro-4-methyl-7-[[[(5-methyl-1H-imidazo[4,5-b]pyridin-2-yl]methyl]amino]carbonyl]-3-oxo-1H-1,4-benzodiazepine-2-acetic acid;

I19)

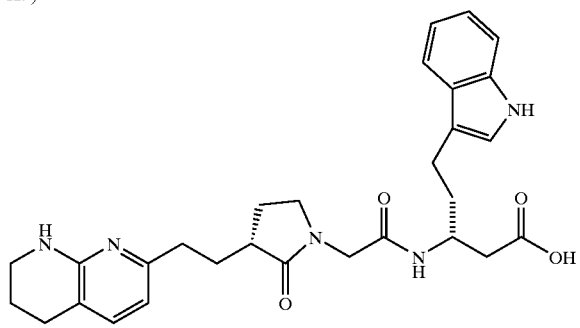

(bR)-b-[[[(3R)-2-oxo-3-[2-(1,5,6,7-tetrahydro-1,8-naphthyridin-2-yl)ethyl]-1-pyrrolidinyl]acetyl]amino]-1H-indole-3-pentanoic acid;

I23)

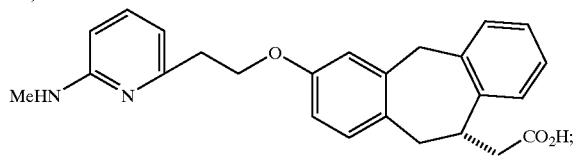

I24) Vitaxin antibody(Ixsys);

I25) Merck KGaA EMD-121974, cyclo[RGDf-N(Me)V-];

I27)

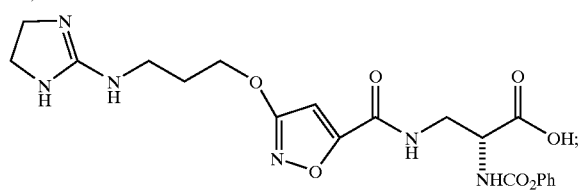

I34)

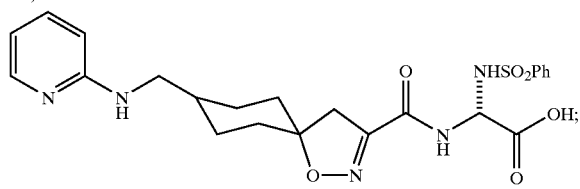

I35)

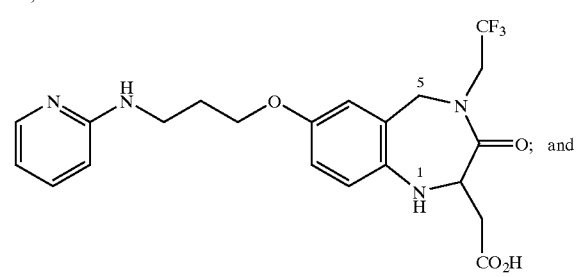

-continued

I36)

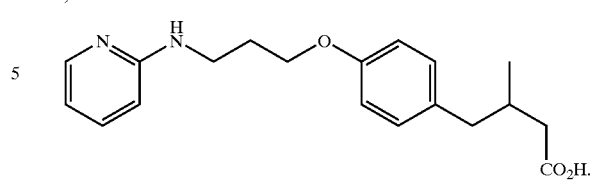

Dosage of Integrin Antagonists

Dosage levels of integrin antagonists on the order of about 0.1 mg to about 10,000 mg of the active ingredient compound are useful in the treatment of the above conditions, with preferred levels of about 1.0 mg to about 1,000 mg. The amount of active ingredient that may be combined with other anticancer agents to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

Treatment dosages generally may be titrated to optimize safety and efficacy. Typically, dosage-effect relationships from in vitro initially can provide useful guidance on the proper doses for patient administration.

Studies in animal models also generally may be used for guidance regarding effective dosages for treatment of cancers in accordance with the present invention. In terms of treatment protocols, it should be appreciated that the dosage to be administered will depend on several factors, including the particular agent that is administered, the route administered, the condition of the particular patient, etc. Generally speaking, one will desire to administer an amount of the compound that is effective to achieve a serum level commensurate with the concentrations found to be effective in vitro. Thus, where an compound is found to demonstrate in vitro activity at, e.g., 10 $\mu$M, one will desire to administer an amount of the drug that is effective to provide about a 10 $\mu$M concentration in vivo. Determination of these parameters are well within the skill of the art.

These considerations, as well as effective formulations and administration procedures are well known in the art and are described in standard textbooks.

Administration Regimen

Any effective treatment regimen can be utilized and readily determined and repeated as necessary to effect treatment. In clinical practice, the compositions containing a integrin antagonist alone or in combination with other therapeutic agents are administered in specific cycles until a response is obtained.

For patients who initially present without advanced or metastatic cancer, an integrin antagonist in combination with radiation therapy, is used as a continuous post-treatment therapy in patients at risk for recurrence or metastasis (for example, in adenocarcinoma of the prostate, risk for metastasis is based upon high PSA, high Gleason's score, locally extensive disease, and/or pathological evidence of tumor invasion in the surgical specimen). The goal in these patients is to inhibit the growth of potentially metastatic cells from the primary tumor during surgery and inhibit the growth of tumor cells from undetectable residual primary tumor.

For patients who initially present with advanced or metastatic cancer, an integrin antagonist in combination with radiation therapy of the present invention is used as a continuous supplement to, or possible replacement for hormonal ablation. The goal in these patients is to slow or prevent tumor cell growth from both the untreated primary tumor and from the existing metastatic lesions.

Illustrations

The following discussion highlights some agents in this respect, which are illustrative, not limitative. A wide variety of other effective agents also may be used.

Colorectal Cancer

The preferred combination therapy for the treatment of colorectal cancer is surgery, followed by a regimen of one or more chemotherapeutic agents, cycled over a one year time period. In the treatment of colorectal cancer, radiation alone or in combination with surgery and/or chemotherapeutic agents is often used. Preferred chemotherapeutic agents include fluorouracil, and Levamisole. Preferably, fluorouracil and Levamisole are used in combination.

Prostate Cancer

Current therapies for prostate cancer focus upon reducing levels of dihydrotestosterone to decrease or prevent growth of prostate cancer. Radiation alone or in combination with surgery and/or chemotherapeutic agents is often used.

Pancreas Cancer

Preferred combinations of therapy for the treatment of non-metastatic adenocarcinoma include the use of preoperative bilary tract decompression (patients presenting with obstructive jaundice); surgical resection, including standard resection, extended or radial resection and distal pancreatectomy (tumors of body and tail); adjuvant radiation; and chemotherapy. For the treatment of metastatic adenocarcinoma, the preferred chemotherapy consists of 5-fluorouracil, followed weekly cisplatin therapy.

Lung Cancer

In many countries including Japan, Europe and America, the number of patients with lung cancer is fairly large and continues to increase year after year and is the most frequent cause of cancer death in both men and women. Although there are many potential causes for lung cancer, tobacco use, and particularly cigarette smoking, is the most important. Additionally, etiologic factors such as exposure to asbestos, especially in smokers, or radon are contributory factors. Also occupational hazards such as exposure to uranium have been identified as an important factor. Finally, genetic factors have also been identified as another factor that increase the risk of cancer.

Lung cancers can be histologically classified into non-small cell lung cancers (e.g. squamous cell carcinoma (epidermoid), adenocarcinoma, large cell carcinoma (large cell anaplastic), etc.) and small cell lung cancer (oat cell). Non-small cell lung cancer (NSCLC) has different biological properties and responses to chemotherapeutics from those of small cell lung cancer (SCLC). Thus, chemotherapeutic formulas and radiation therapy are different between these two types of lung cancer.

Non-small Cell Lung Cancer

Where the location of the non-small cell lung cancer tumor can be easily excised (stage I and II disease) surgery is the first line of therapy and offers a relatively good chance for a cure. However, in more advanced disease (stage IIIa and greater), where the tumor has extended to tissue beyond the bronchopulmonary lymph nodes, surgery may not lead to complete excision of the tumor. In such cases, the patient's chance for a cure by surgery alone is greatly diminished. Where surgery will not provide complete removal of the NSCLC tumor, other types of therapies must be utilized.

Today radiation therapy is the standard treatment to control unresectable or inoperable NSCLC. Improved results have been seen when radiation therapy has been combined with chemotherapy, but gains have been modest and the search continues for improved methods of combining modalities.

Radiation therapy is based on the principle that high-dose radiation delivered to a target area will result in the death of reproductive cells in both tumor and normal tissues. The radiation dosage regimen is generally defined in terms of radiation absorbed dose (rad), time and fractionation, and must be carefully defined by the oncologist. The amount of radiation a patient receives will depend on various consideration but the two most important considerations are the location of the tumor in relation to other critical structures or organs of the body, and the extent to which the tumor has spread. A preferred course of treatment for a patient undergoing radiation therapy for NSCLC will be a treatment schedule over a 5 to 6 week period, with a total dose of 50 to 60 Gy administered to the patient in a single daily fraction of 1.8 to 2.0 Gy, 5 days a week. A Gy is an abbreviation for Gray and refers to 100 rad of dose.

However, as NSCLC is a systemic disease, and radiation therapy is a local modality, radiation therapy as a single line of therapy is unlikely to provide a cure for NSCLC, at least for those tumors that have metastasized distantly outside the zone of treatment. Thus, the use of radiation therapy with other modality regimens have important beneficial effects for the treatment of NSCLC.

Generally, radiation therapy has been combined temporally with chemotherapy to improve the outcome of treatment. There are various terms to describe the temporal relationship of administering radiation therapy and chemotherapy, and the following examples are the preferred treatment regimens and are generally known by those skilled in the art and are provided for illustration only and are not intended to limit the use of other combinations. "Sequential" radiation therapy and chemotherapy refers to the administration of chemotherapy and radiation therapy separately in time in order to allow the separate administration of either chemotherapy or radiation therapy. "Concomitant" radiation therapy and chemotherapy refers to the administration of chemotherapy and radiation therapy on the same day. Finally, "alternating" radiation therapy and chemotherapy refers to the administration of radiation therapy on the days in which chemotherapy would not have been administered if it was given alone.

It is reported that advanced non-small cell lung cancers do not respond favorably to single-agent chemotherapy and useful therapies for advanced inoperable cancers have been limited. (J. Clin. Oncol. 1992, 10, 829–838).

Japanese Patent Kokai 5-163293 refers to 16-membered-ring macrolide antibiotics as a drug delivery carrier capable of transporting anthoracycline-type anticancer drugs into the lungs for the treatment of lung cancers. However, the macrolide antibiotics specified herein are disclosed to be only a drug carrier, and there is no reference to the therapeutic use of macrolides against non-small cell lung cancers.

WO 93/18652 refers to the effectiveness of the specified 16-membered-ring macrolides such as bafilomycin, etc. in treating non-small cell lung cancers, but they have not yet been clinically practicable.

Pharmacology, vol. 41, pp. 177–183 (1990) describes that a long-term use of erythromycin increases productions of interleukins 1, 2 and 4, all of which contribute to host immune responses, but there is no reference to the effect of this drug on non-small cell lung cancers.

Tetragenesis, Carcinogenesis, and Mutagenesis, vol. 10, pp. 477–501 (1990) describes that some of antimicrobial drugs can be used as an anticancer agent, but does not refer to their application to non-small cell lung cancers.

In addition, interleukins are known to have an antitumor effect, but have not been reported to be effective against non-small cell lung cancers.

Any 14- or 15-membered-ring macrolides have not been reported to be effective against non-small cell lung cancers.

However, several chemotherapeutic agents have been shown to be efficacious against NSCLC. Preferred chemotherapeutic agents against NSCLC include etoposide, carboplatin, methotrexate, 5-fluorouracil, epirubicin, doxorubicin, and cyclophosphamide. The most preferred chemotherapeutic agents active against NSCLC include cisplatin, ifosfamide, mitomycin C, epirubicin, vinblastine, and vindesine.

Other agents that are under investigation for use against NSCLC include: camptothecins, a topoisomerase 1 inhibitor; navelbine (vinorelbine), a microtubule assebly inhibitor; taxol, inhibitor of normal mitotic activity; gemcitabine, a deoxycytidine analogue; fotemustine, a nitrosourea compound; and edatrexate, a antifol.

The overall and complete response rates for NSCLC has been shown to increase with use of combination chemotherapy as compared to single-agent treatment. Haskel, Chest. 1991, 99: 1325; Bakowsk, Cancer Treat. Rev. 1983, 10:159; Joss, Cancer Treat. Rev. 1984, 11: 205.

Small Cell Lung Cancer

Approximately 15 to 20 percent of all cases of lung cancer reported worldwide is small cell lung cancer (SCLC). (Ihde, *Cancer* 1984, 54, 2722). Currently, treatment of SCLC incorporates multi-modal therapy, including chemotherapy, radiation therapy and surgery. Response rates of localized or disseminated SCLC remain high to systemic chemotherapy, however, persistence of the primary tumor and persistence of the tumor in the associated lymph nodes has led to the integration of several therapeutic modalities in the treatment of SCLC.

The most preferred chemotherapeutic agents against SCLC include vincristine, cisplatin, carboplatin, cyclophosphamide, epirubicin (high dose), etoposide (VP-16) I.V., etoposide (VP-16) oral, isofamide, teniposide (VM-26), and doxorubicin. Preferred single-agents chemotherapeutic agents include BCNU (carmustine), vindesine, hexamethylmelamine (altretamine), methotrexate, nitrogen mustard, and CCNU (lomustine).

Other chemotherapeutic agents under investigation that have shown activity againe SCLC include iroplatin, gemcitabine, lonidamine, and taxol. Single-agent chemotherapeutic agents that have not shown activity against SCLC include mitoguazone, mitomycin C, aclarubicin, diaziquone, bisantrene, cytarabine, idarubicin, mitomxantrone, vinblastine, PCNU and esorubicin.

The poor results reported from single-agent chemotherapy has led to use of combination chemotherapy.

Additionally, radiation therapy in conjunction with integrin antagonists and systemic chemotherapy is contemplated to be effective at increasing the response rate for SCLC patients. The typical dosage regimen for radiation therapy ranges from 40 to 55 Gy, in 15 to 30 fractions, 3 to 7 times week. The tissue volume to be irradiated is determined by several factors and generally the hilum and subcarnial nodes, and bialteral mdiastinal nodes up to the thoracic inlet are treated, as well as the primary tumor up to 1.5 to 2.0 cm of the margins.

Breast Cancer

Today, among women in the United States, breast cancer remains the most frequent diagnoses cancer. One in 8 women in the United States at risk of developing breast cancer in their lifetime. Age, family history, diet, and genetic factors have been identified as risk factors for breast cancer. Breast cancer is the second leading cause of death among women.

Different chemotherapeutic agents are known in the art for treating breast cancer. Cytotoxic agents used for treating breast cancer include doxorubicin, cyclophosphamide, methotrexate, 5-fluorouracil, mitomycin C, mitoxantrone, taxol, and epirubicin. (CANCER SURVEYS, Breast Cancer volume 18, Cold Spring Harbor Laboratory Press, 1993).

In the treatment of locally advanced noninflammatory breast cancer, an integrin antagonist and radiation therapy can be used to treat the disease in combination with other antiangiogenic agents, or in combination with surgery, or with chemotherapeutic agents. Preferred combinations of chemotherapeutic agents, and surgery that can be used in combination with the radiation therapy and integrin antagonists include, but are not limited to: 1) doxorubicin, vincristine; 2) cyclophosphamide, doxorubicin, 5-flourouracil, vincristine, prednisone; 3) cyclophosphamide, doxorubicin, 5-flourouracil, premarin, tamoxifen; 4) cyclophosphamide, doxorubicin, 5-flourouracil, premarin, tamoxifen, mastectomy; 5) mastectomy, levamisole; 6) mastectomy; and 7) mastecomy, cyclophosphamide, doxorubicin, 5-fluorouracil, tamoxifen, halotestin.

In the treatment of locally advanced inflammatory breast cancer, integrin antagonists and radiation therapy can be used to treat the disease in combination with other antiangiogenic agents, or in combination with surgery, or with chemotherapeutic agents. Preferred combinations of chemotherapeutic agents, radiation therapy and surgery that can be used in combination with the integrin antagonists and radiation include, but or not limited to: 1) cyclophosphamide, doxorubicin, 5-fluorouracil; 2) cyclophosphamide, doxorubicin, 5-fluorouracil, mastectomy; 3) 5-fluruoracil, doxorubicin, clyclophosphamide, vincristine, prednisone, mastectomy; 4) 5-flurouracil, doxorubicin, clyclophosphamide, vincristine, mastectomy; 5) cyclophosphamide, doxorubicin, 5-fluorouracil, vincristine; 6) cyclophosphamide, doxorubicin, 5-fluorouracil, vincristine, mastectomy; 7) doxorubicin, vincristine, methotrexate, followed by vincristine, cyclophosphamide, 5-florouracil; 8) doxorubicin, vincristine, cyclophosphamide, methotrexate, 5-florouracil, followed by vincristine, cyclophosphamide, 5-florouracil; 9). surgery, followed by cyclophosphamide, methotrexate, 5-fluorouracil, predinsone, tamoxifen, followed by cyclophosphamide, methotrexate, 5-fluorouracil, predinsone, tamoxifen, doxorubicin, vincristine, tamoxifen; 10) surgery, followed by cyclophosphamide, methotrexate, 5-fluorouracil, followed by cyclophosphamide, methotrexate, 5-fluorouracil, predinsone, tamoxifen, doxorubicin, vincristine, tamoxifen; 11) surgery, followed by cyclophosphamide, methotrexate, 5-fluorouracil, predinsone, tamoxifen, followed by cyclophosphamide, methotrexate, 5-fluorouracil, doxorubicin, vincristine, tamoxifen;; 12) surgery, followed by cyclophosphamide, methotrexate, 5-fluorouracil, followed by cyclophosphamide, methotrexate, 5-fluorouracil, predinsone, tamoxifen, doxorubicin, vincristine; 13) surgery, followed by cyclophosphamide, methotrexate, 5-fluorouracil, predinsone, tamoxifen, followed by cyclophosphamide, methotrexate, 5-fluorouracil, predinsone, tamoxifen, doxorubicin, vincristine, tamoxifen; 14) surgery, followed by cyclophosphamide, methotrexate, 5-fluorouracil, followed by cyclophosphamide, methotrexate, 5-fluorouracil, predinsone, tamoxifen, doxorubicin, vincristine; 15) surgery, followed by cyclophosphamide, methotrexate, 5-fluorouracil, predinsone, tamoxifen, followed by cyclophosphamide, methotrexate, 5-fluorouracil, doxorubicin, vincristine; 16) 5-florouracil, -doxorubicin, cyclophosphamide followed by mastectomy, followed by 5-florouracil, doxorubicin, cyclophosphamide.

In the treatment of metastatic breast cancer, radiation therapy and integrin antagonists are used to treat the disease in combination with surgery, or with chemotherapeutic agents. Preferred combinations of chemotherapeutic agents, and surgery that can be used in combination with the radiation therapy and integrin antagonists include, but are not limited to: 1) cyclosphosphamide, methotrexate, 5-fluorouracil; 2) cyclophosphamide, adriamycin, 5-fluorouracil; 3) cyclosphosphamide, methotrexate, 5-flurouracil, vincristine, prednisone; 4) adriamycin, vincristine; 5) thiotepa, adriamycin, vinblastine; 6) mitomycin, vinblastine; 7) cisplatin, etoposide.

Bladder Cancer

The classification of bladder cancer is divided into three main classes: 1) superficial disease, 2) muscle-invasive disease, and 3) metastatic disease.

Currently, transurethral resection (TUR), or segmental resection, account for first line therapy of superficial bladder cancer, i.e., disease confined to the mucosa or the lamina propria. However, intravesical therapies are necessary, for example, for the treatment of high-grade tumors, carcinoma in situ, incomplete resections, recurrences, and multifocal papillary. Recurrence rates range from up to 30 to 80 percent, depending on stage of cancer.

Therapies that are currently used as intravesical therapies include chemotherapy, immuontherapy, bacille Calmette-Guerin (BCG) and photodynamic therapy. The main objective of intravesical therapy is twofold: to prevent recurrence in high-risk patients and to treat disease that cannot by resected. The use of intravesical therapies must be balanced with its potentially toxic side effects. Additionally, BCG requires an unimpaired immune system to induce an anti-tumor effect. Chemotherapeutic agents that are known to be inactive against superficial bladder cancer include Cisplatin, actinomycin D, 5-fluorouracil, bleomycin, and cyclophosphamide methotrxate.

In the treatment of superficial bladder cancer, integrin antagonists and radiation therapy are used to treat the disease in combination with surgery (TUR), and intravesical therapies.

Preferred combinations of chemotherapeutic agents are selected from the group consisting of thiotepa (30 to 60 mg/day), mitomycin C (20 to 60 mg/day), and doxorubicin (20 to 80 mg/day).

The preferred intravesicle immunotherapuetic agent that may be used in the present invention is BCG. The preferred daily dose ranges from 60 to 120 mg, depending on the strain of the live attenuated tuberculosis organism used.

The preferred photodynamic therapuetic agent that may be used with the present invention is Photofrin I, a photosensitizing agent, administered intravenously. It is taken up by the low-density lipoprotein receptors of the tumor cells and is activated by exposure to visible light. Additionally, neomydium YAG laser activation generates large amounts of cytotoxic free radicals and singlet oxygen.

In the treatment of muscle-invasive bladder cancer, radiation therapy and integrin antagonists can be used to treat the disease in combination with other antiangiogenic agents, or in combination with surgery (TUR), intravesical chemotherapy, and radical cystectomy with pelvic lymph node dissection.

The preferred radiation dose is between 5,000 to 7,000 cGY in fractions of 180 to 200 cGY to the tumor. Additionally, 3,500 to 4,700 cGY total dose is administered to the normal bladder and pelvic contents in a four-field technique. Radiation therapy should be considered only if the patient is not a surgical candidate, but may be considered as preoperative therapy.

The preferred combination of chemotherapeutic agents that can be used in combination with radiation therapy and integrin antagonists is cisplatin, methotrexate, vinblastine.

Currently no curative therapy exists for metastatic bladder cancer. The present invention contemplates an effective treatment of bladder cancer leading to improved tumor inhibition or regression, as compared to current therapies.

In the treatment of metastatic bladder cancer, a combination of radiation therapy and integrin antagonists can be used to treat the disease in combination with surgery, or with chemotherapeutic agents.

Preferred combinations of chemotherapeutic agents include, but are not limited to: 1) cisplatin and methotrexate; 2) doxorubicin, vinblastine, cyclophoshamide, and 5-fluorouracil; 3) vinblastine, doxorubicin, cisplatin, methotrexate; 4) vinblastine, cisplatin, methbtrexate; 5) cyclophosphamide, doxorubicin, cisplatin; 6) 5-fluorouracil, cisplatin.

Head and Neck Cancers

Head and neck cancer accounts for approximately 2% of new cancer cases in the United States. Common intracranial neoplasms include glioma, meningioma, neurinoma, and adenoma. Preferred combinations that can be used along with a combination of radiation therapy and an integrin antagonist for the treatment of malignant glioma include: 1) BCNU (carmustine); 2) methyl CCNU (lomustine); 3) medrol; 4) procarbazine; 5) BCNU, medrol; 6) misonidazole, BCNU; 7) streptozotocin; 8) BCNU, procarbazine; 9) BCNU, hydroxyurea, procarbazine, VM-26; 10) BNCU, 5-flourouacil; 11) methyl CCNU, dacarbazine; 12) misonidazole, BCNU; and 13) PCNU. The preferred dose of radiation therapy is about 5,500 to about 6,000 cGY. Preferred radiosensitizers include misonidazole, intra-arterial Budr and intravenous iododeoxyuridine (IUdR).

Biological Evaluation

Solitary tumors are generated in the right hind legs of mice by the injection of $3\times10^5$ viable NFSA tumor cells. Treatment with an integrin antagonist (6 mg/kg body weight) or vehicle (0.05% Tween 20 and 0.95% polyethylene glycol) given in the drinking water is started when tumors are approximately 6 mm in diameter and the treatment is continued for 10 consecutive days. Water bottles are changed every 3 days. Tumor irradiation is performed 3–8 days after initiation of the treatment with an integrin antagonist. The end points of the treatment are tumor growth delay (days) and $TCD_{50}$ (tumor control dose 50, defined as the radiation dose yielding local tumor cure in 50% of irradiated mice 120 days after irradiation). To obtain tumor growth curves, three mutually orthogonal diameters of tumors are measured daily with a vernier caliper, and the mean values are calculated.

Local tumor irradiation with single γ-ray doses of 30, 40, or 50 Gy is given when these tumors reach 8 mm in diameter. Irradiation to the tumor is delivered from a dual-source $^{137}$Cs irradiator at a dose rate of 6.31 Gy/minute. During irradiation, unanesthetized mice are immobilized on a jig and the tumor is centered in a circular radiation field 3 cm in diameter. Regression and regrowth of tumors are followed at 1–3 day intervals until the tumor diameter reaches approximately 14 mm.

What is claimed is:

1. A method for treating neoplasia in a subject in need of such treatment, the method comprises treating the subject with radiation therapy and a therapeutically effective amount of a integrin antagonist or pharmaceutically-acceptable or derivative thereof, wherein the integrin antagonist is selected from compounds, and their pharmaceutically acceptable salts, of the group consisting of:

1)

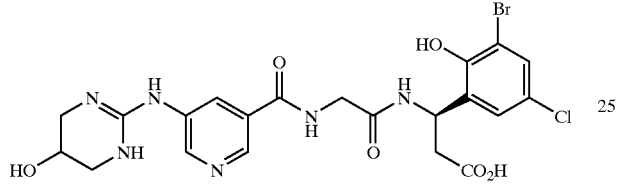

(3R)-N-[[5-[(1,4,5,6-tetrahydro-5-hydroxy-2-pyrimidinyl)amino]-3-pyridinyl]carbonyl]glycyl-3-(3-bromo-5-chloro-2-hydroxyphenyl)-b-alanine;

2)

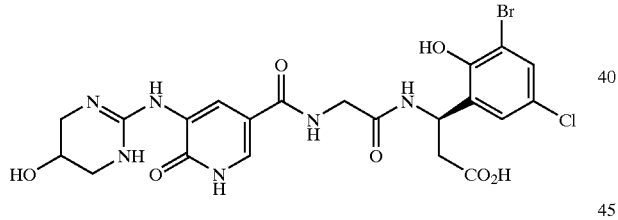

(3R)-N-[[1,6-dihydro-6-oxo-5-[(1,4,5,6-tetrahydro-5-hydroxy-2-pyrimidinyl)amino]-3-pyridinyl]carbonyl]glycyl-3-(3-bromo-5-chloro-2-hydroxyphenyl)-b-alanine;

3)

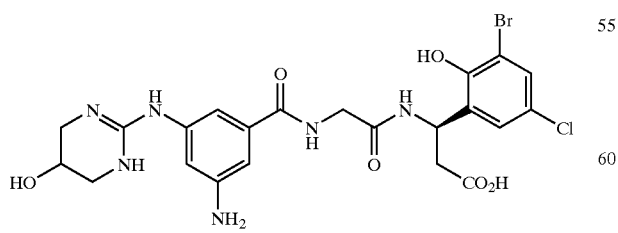

(3R)-N-[3-amino-5-[(1,4,5,6-tetrahydro-5-hydroxy-2-pyrimidinyl)amino]benzoyl}glycyl-3-(3-bromo-5-chloro-2-hydroxyphenyl)-b-alanine;

4)

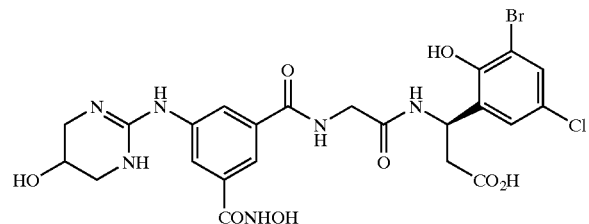

(3R)-N-[3-[(hydroxyamino)carbonyl]-5-[(1,4,5,6-tetrahydro-5-hydroxy)-2-pyrimidinyl)amino]benzoyl]glycyl-3-(3-bromo-5-chloro-2-hydroxyphenyl)-b-alanine;

5)

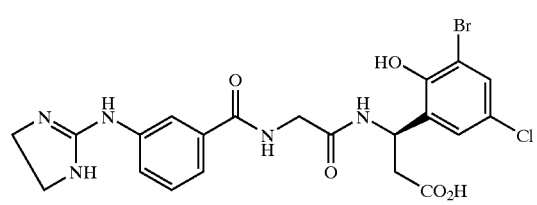

(3R)-N-[3-[(4-,5-dihydro-1H-imidazol-2-yl)amino]benzoyl]glycyl-3-(3-bromo-5-chloro-2-hydroxyphenyl)-b-alanine;

6)

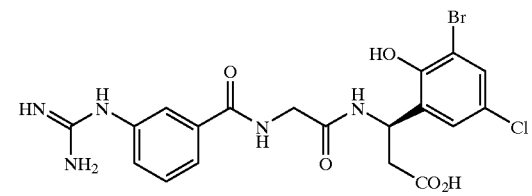

(3R)-N-[3-[(aminoiminomethyl)amino]benzoyl]glycyl-3-(3-bromo-5-chloro-2-hydroxyphenyl)-b-alanine;

7)

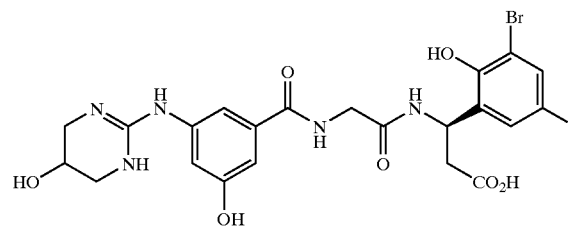

(3R)-N-[3-hydroxy-5-[(1,4,5,6-tetrahydro-5-hydroxy-2-pyrimidinyl)amino]benzoyl]glycyl-3-(3-bromo-5-chloro-2-hydroxyphenyl)-b-alanine;

8)

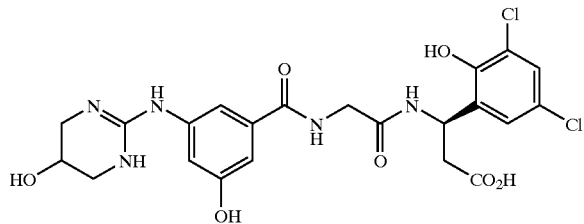

(3R)-N-[3-hydroxy-5-[(1,4,5,6-tetrahydro-5-hydroxy-2-pyrimidinyl)amino]benzoyl]glycyl-3-(3,5-dichloro-2-hydroxyphenyl)-b-alanine;

9)

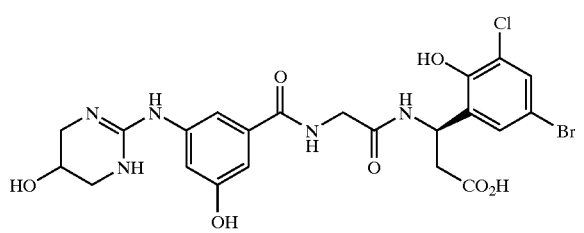

(3R)-N-[3-hydroxy-5-[(1,4,5,6-tetrahydro-5-hydroxy-2-pyrimidinyl)amino]benzoyl]glycyl-3-(5-bromo-3-chloro-2-hydroxyphenyl)-b-alanine;

10)

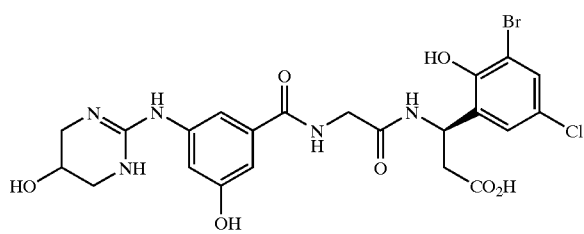

(3R)-N-[3-hydroxy-5-[(1,4,5,6-tetrahydro-5-hydroxy-2-pyrimidinyl)amino]benzoyl]glycyl-3-(3-bromo-5-chloro-2-hydroxyphenyl)-b-alanine;

11)

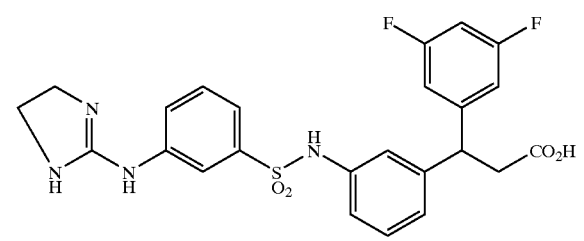

b-[3-[[[3-[[4,5-dihydro-1H-imidazol-2-yl)amino]phenyl]sulfonyl]amino]phenyl]-3,5-difluorobenzenepropanoic acid;

12)

3,5-difluoro-b-[3-[[[3-[(1,4,5,6-tetrahydro-2-pyrimidinyl)amino]benzoyl]amino]methyl]phenyl]benzenepropanoic acid;

13)

(2E)-3-[3-ethyl-4-[[3-[(1,4,5,6-tetrahydro-2-pyrimidinyl)amino]benzoyl]amino]phenyl]-2-propenoic acid;

14)

(2E)-3-[3-ethyl-4-[[3-[(1,4,5,6-tetrahydro-2-pyrimidinyl)amino]benzoyl]amino]phenyl]-2-propenoic acid;

15)

(2E)-3-[3-[2-[3-[(4,5-dihydro-1H-imidazol-2-yl)amino]phenyl]-2-oxoethoxy]phenyl]-2-propenoic acid;

16)

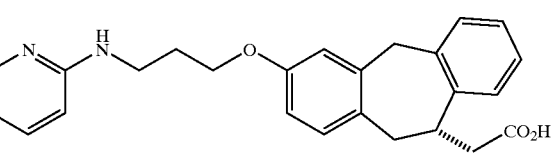

(10S)-10,11-dihydro-3-[3-(2-pyridinylamino)propoxy]-5H-dibenzo[a,d]cycloheptene-10-acetic acid;

17)
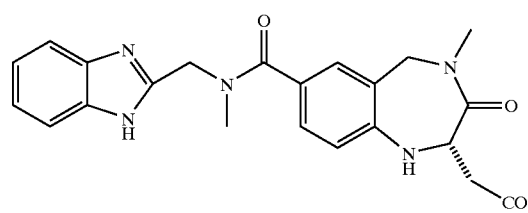
(2S)-7-[[(1H-benzimidazol-2-ylmethyl)methylamino]carbonyl]-2,3,4,5-tetrahydro-4-methyl-3-oxo-1H-1,4-benzodiazepine-2-acetic acid;
18)
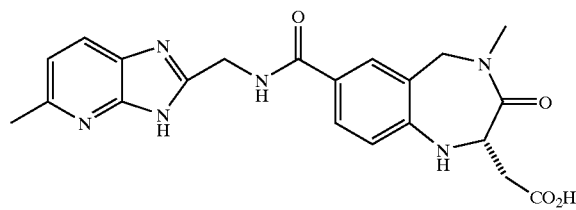
(2S)-2,3,4,5-tetrahydro-4-methyl-7-[[[(5-methyl-1H-imidazo[4,5-b]pyridin-2-yl]methyl]amino]carbonyl]-3-oxo-1H-1,4-benzodiazepine-2-acetic acid;
19)
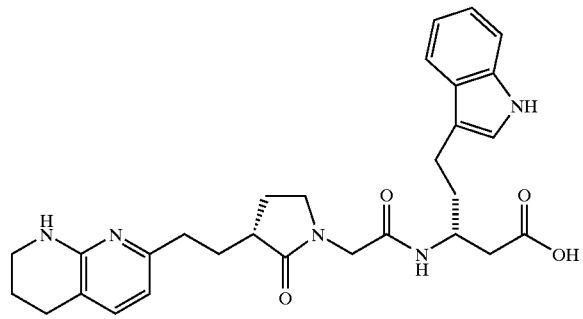
(bR)-b-[[[(3R)-2-oxo-3-[2-(1,5,6,7-tetrahydro-1,8-naphthyridin-2-yl)ethyl]-1-pyrrolidinyl]acetyl]amino]-1H-indole-3-pentanoic acid,
20)
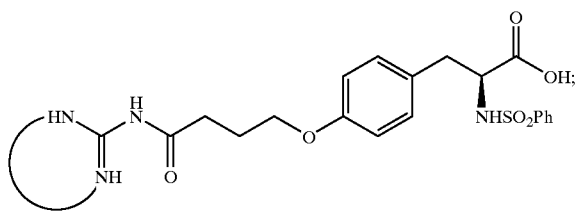
21)
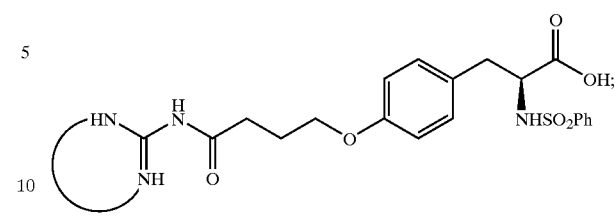
22)
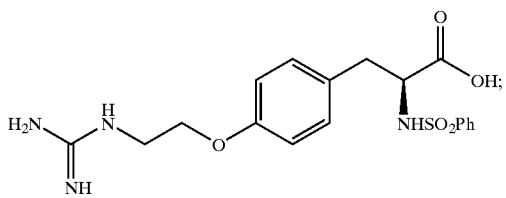
23)
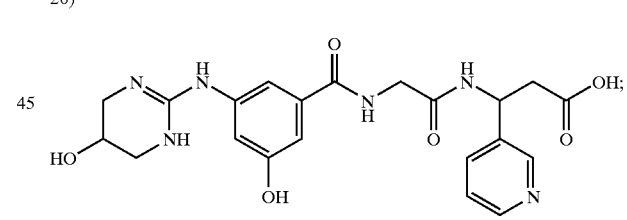
24) Vitaxin antibody;
25) Merck KGaA EMD-121974, cyclo[RGDf-N(Me)V-];
26)
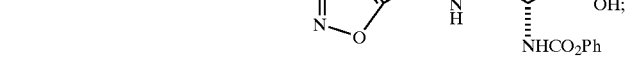
27)
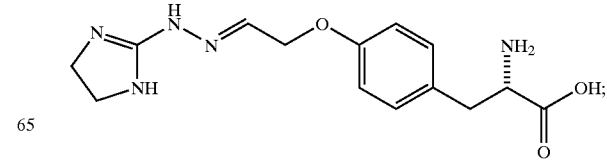
28)

29) 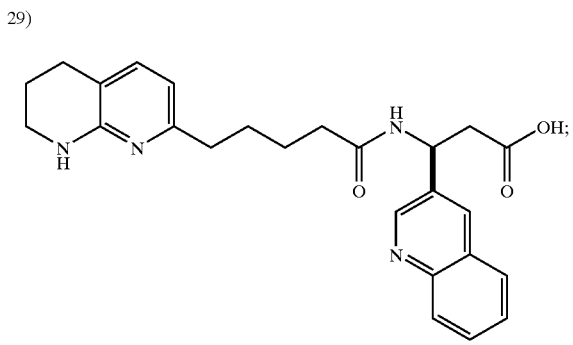
30) 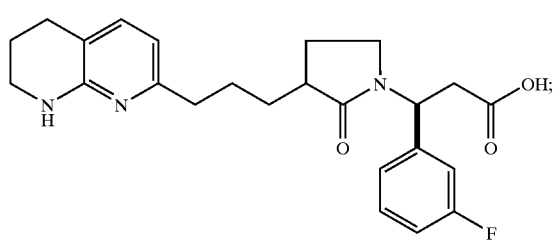
31) 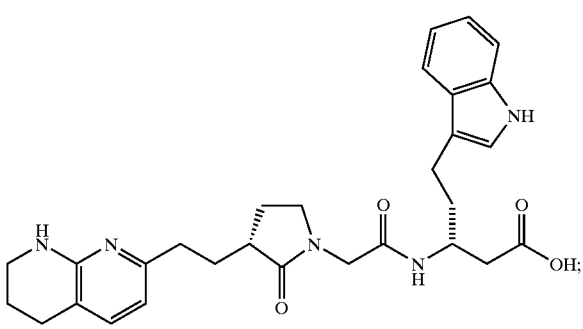
32) 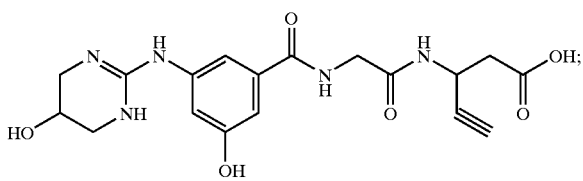
33) 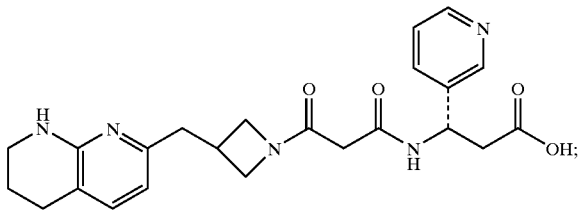
34) 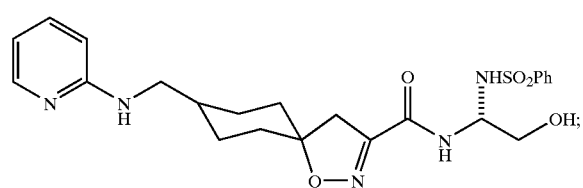
35) 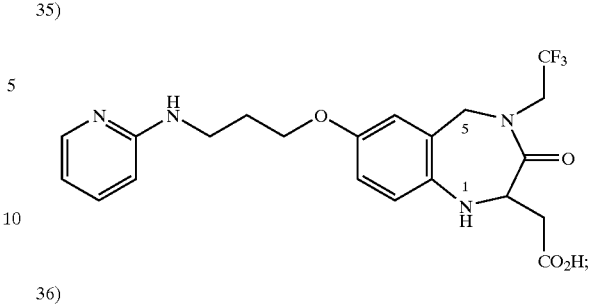
36) 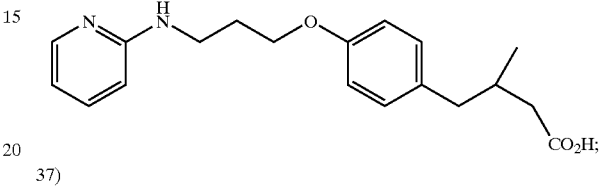
37) 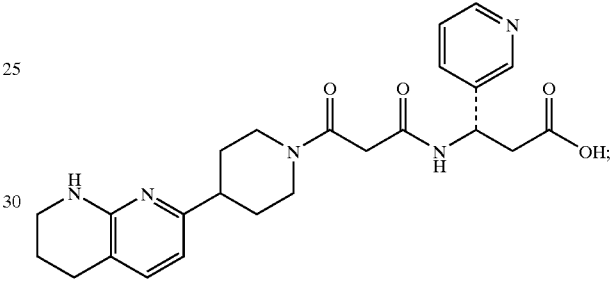
38) 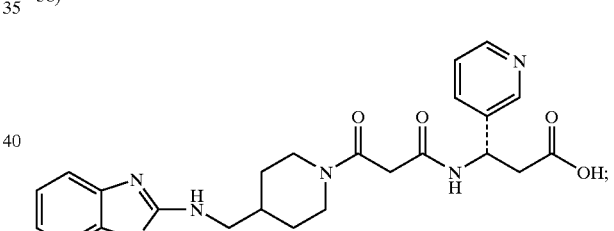
39) 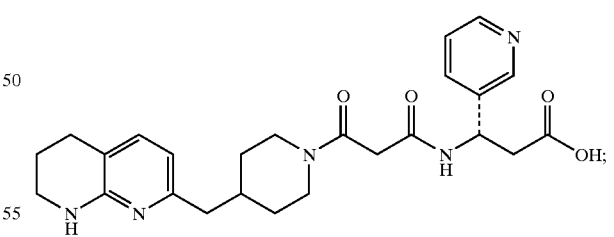
40) 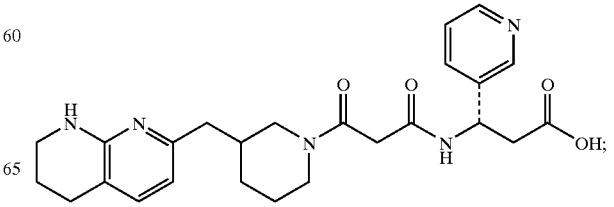

41)

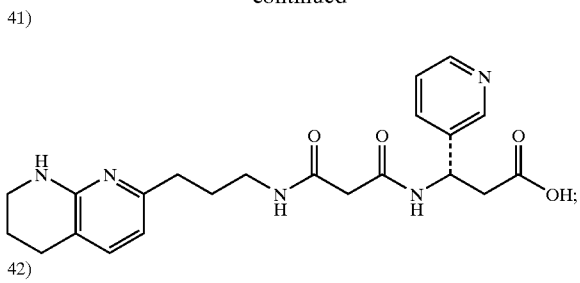

42)

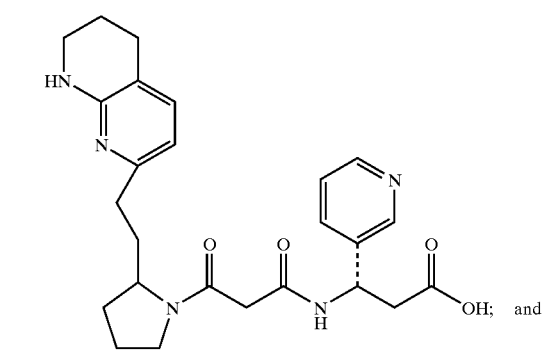

43)

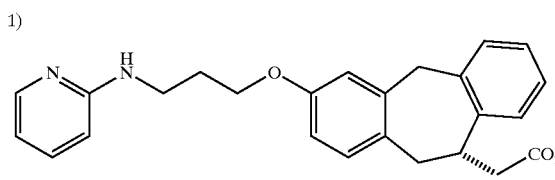

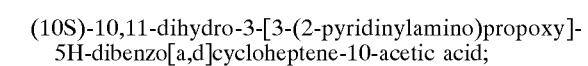

2. A method for treating neoplasia in a subject in need of such treatment, the method comprises treating the subject with radiation therapy and a therapeutically effective amount of a integrin antagonist or pharmaceutically-acceptable or derivative thereof, wherein the integrin antagonist is selected from compounds, and their pharmaceutically acceptable salts, of the group consisting of:

1)

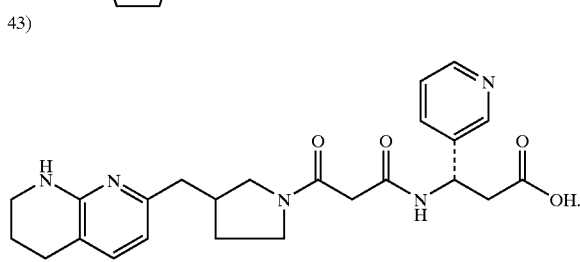

(10S)-10,11-dihydro-3-[3-(2-pyridinylamino)propoxy]-5H-dibenzo[a,d]cycloheptene-10-acetic acid;

2)

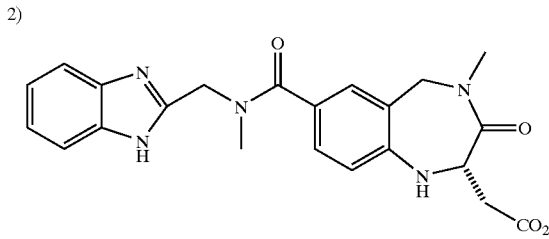

(2S)-7-[[(1H-benzimidazol-2-ylmethyl)methylamino]carbonyl]-2,3,4,5-tetrahydro-4-methyl-3-oxo-1H-1,4-benzodiazepine-2-acetic acid;

3)

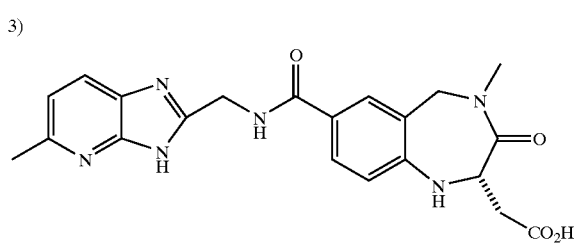

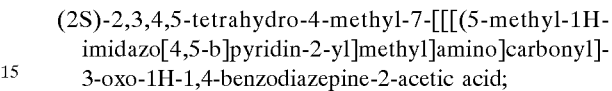

(2S)-2,3,4,5-tetrahydro-4-methyl-7-[[[(5-methyl-1H-imidazo[4,5-b]pyridin-2-yl]methyl]amino]carbonyl]-3-oxo-1H-1,4-benzodiazepine-2-acetic acid;

4)

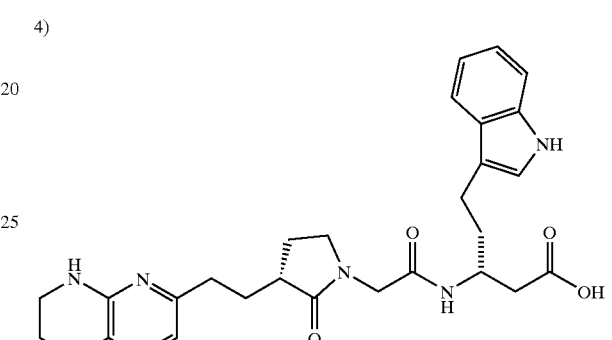

(bR)-b-[[[(3R)-2-oxo-3-[2-(1,5,6,7-tetrahydro-1,8-naphthyridin-2-yl)ethyl]-1-pyrrolidinyl]acetyl]amino]-1H-indole-3-pentanoic acid;

5)

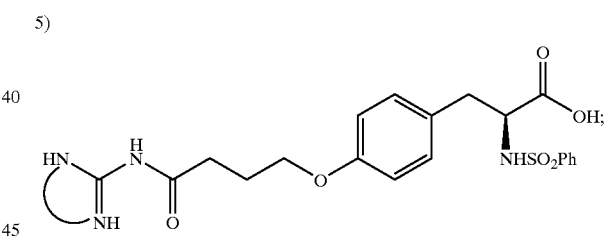

6)

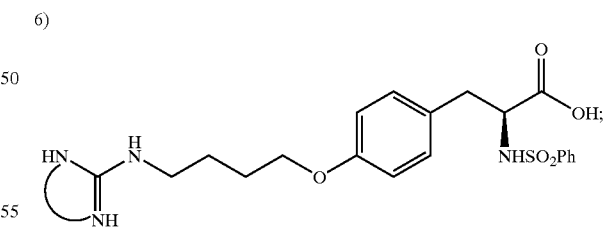

7)

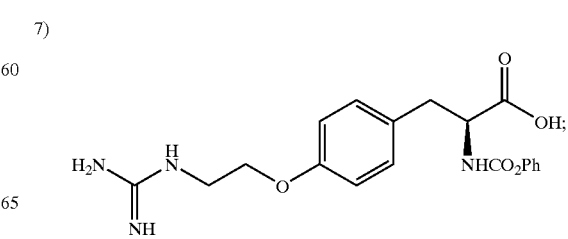

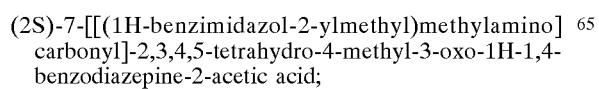

8)

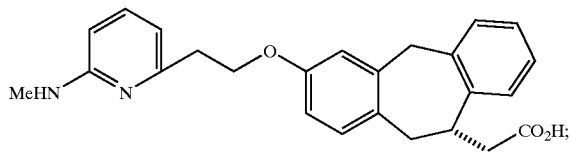

9) Vitaxin antibody;
10) Merck KGaA EMD-121974, cyclo[RGDf-N(Me)V-];

11)

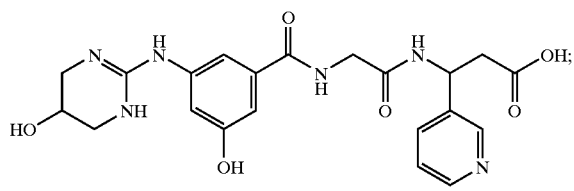

12)

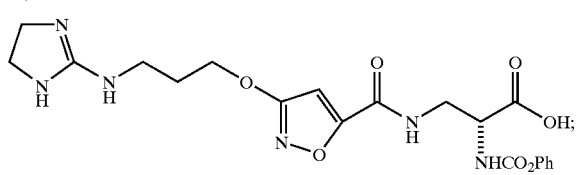

13)

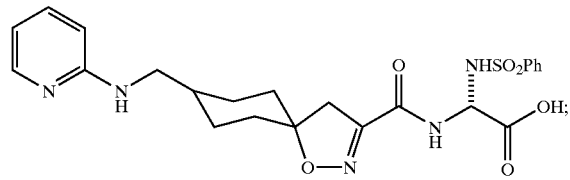

14)

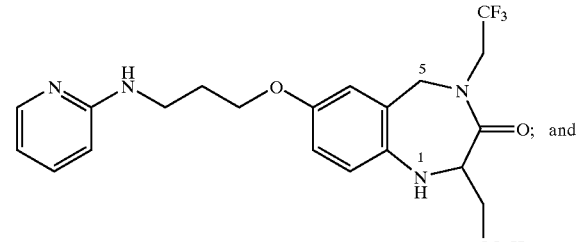

15)

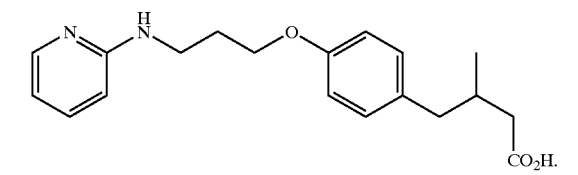

3. The method of claim 2 wherein the integrin antagonist is

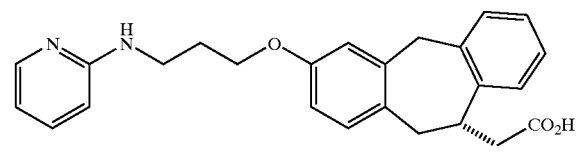

(10S)-10,11-dihydro-3-[3-(2-pyridinylamino)propoxy]-5H-dibenzo[a,d]cycloheptene-10-acetic acid.

4. The method of claim 2 wherein the integrin antagonist is

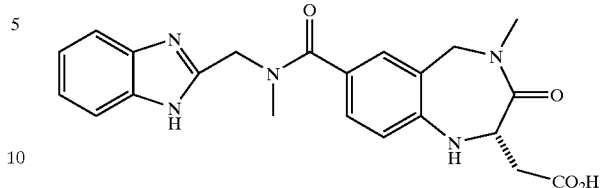

(2S)-7-[[(1H-benzimidazol-2-ylmethyl)methylamino]carbonyl]-2,3,4,5-tetrahydro-4-methyl-3-oxo-1H-1,4-benzodiazepine-2-acetic acid.

5. The method of claim 2 wherein the integrin antagonist is

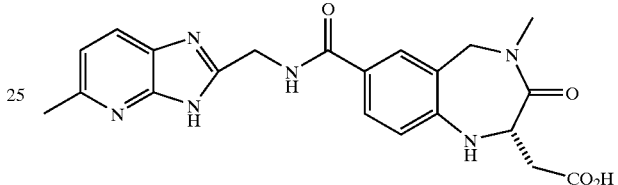

(2S)-2,3,4,5-tetrahydro-4-methyl-7-[[[(5-methyl-1H-imidazo[4,5-b]pyridin-2-yl]methyl]amino]carbonyl]-3-oxo-1H-1,4-benzodiazepine-2-acetic acid.

6. The method of claim 2 wherein the integrin antagonist is

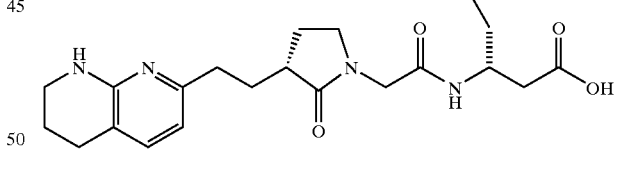

(bR)-b-[[[(3R)-2-oxo-3-[2-(1,5,6,7-tetrahydro-1,8-naphthyridin-2-yl)ethyl]-1-pyrrolidinyl]acetyl]amino]-1H-indole-3-pentanoic acid.

7. The method of claim 2 wherein the integrin antagonist is

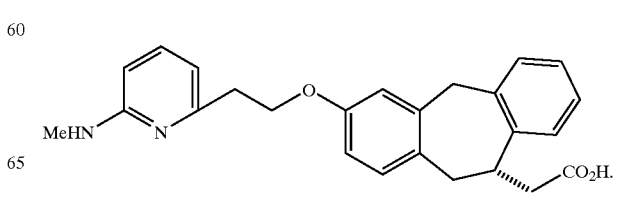

8. The method of claim 2 wherein the integrin antagonist is Vitaxin antibody.

9. The method of claim 2 wherein the integrin antagonist is Merck KGaA EMD-121974, cyclo[RGDf-N(Me) V-].

10. The method of claim 2 wherein the integrin antagonist is

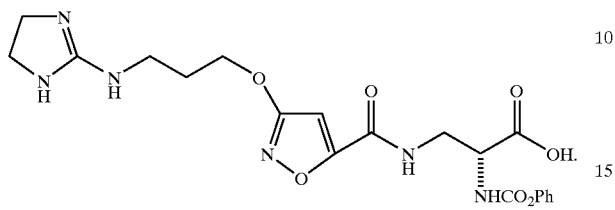

11. The method of claim 2 wherein the integrin antagonist is

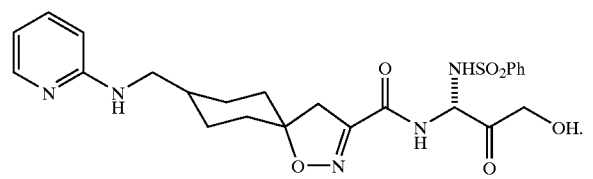

12. The method of claim 2 wherein the integrin antagonist is

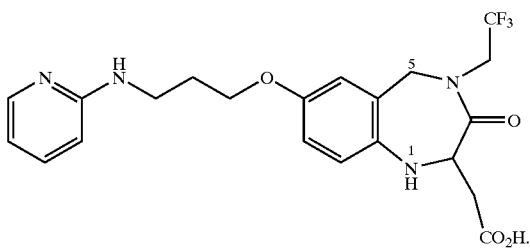

13. The method of claim 2 wherein the integrin antagonist is

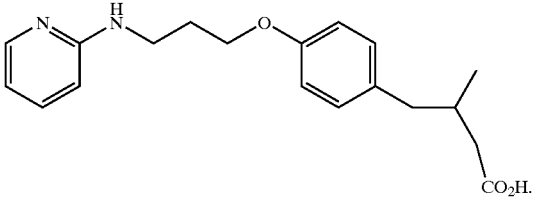

14. The method of claim 1 wherein the combination is administered in a sequential manner.

15. The method of claim 1 wherein the combination is administered in a substantially simultaneous manner.

* * * * *